US010124186B2

(12) United States Patent
McKenna et al.

(10) Patent No.: US 10,124,186 B2
(45) Date of Patent: Nov. 13, 2018

(54) SYSTEM FOR AUTOMATICALLY AMENDING ENERGY FIELD CHARACTERISTICS IN THE APPLICATION OF AN ENERGY FIELD TO A LIVING ORGANISM FOR TREATMENT OF INVASIVE AGENTS

(71) Applicant: Endomagnetics Limited, Cambridge (GB)

(72) Inventors: Daniel B. McKenna, Vail, CO (US); Karl M. Frantz, Broomfield, CO (US)

(73) Assignee: Endomagnetics Limited, Cambridge (GB)

( * ) Notice: Subject to any disclaimer, the term of this patent is extended or adjusted under 35 U.S.C. 154(b) by 322 days.

(21) Appl. No.: 14/757,629

(22) Filed: Dec. 23, 2015

(65) Prior Publication Data

US 2016/0151636 A1    Jun. 2, 2016

Related U.S. Application Data

(63) Continuation of application No. 13/012,539, filed on Jan. 24, 2011.

(51) Int. Cl.
*A61B 5/05* (2006.01)
*A61N 2/00* (2006.01)
(Continued)

(52) U.S. Cl.
CPC ............. *A61N 2/002* (2013.01); *A61B 5/05* (2013.01); *A61B 18/04* (2013.01); *A61N 2/004* (2013.01);
(Continued)

(58) Field of Classification Search
CPC ......... A61B 18/04; A61B 5/0059; A61B 5/05; A61B 5/0515; A61N 2/002; A61N 2/004; A61N 2/02
See application file for complete search history.

(56) References Cited

U.S. PATENT DOCUMENTS 4,346,715 A    8/1982   Gammell
5,099,756 A    3/1992   Franconi et al.
(Continued)

FOREIGN PATENT DOCUMENTS

CN      1694657      11/2005
CN    101854977      10/2010
(Continued)

OTHER PUBLICATIONS

Sophie Laurenta et al. "Magnetic Fluid Hyperthermia: Focus on superparamagnetic iron oxide nanoparticles" Advances in Colloid and Interface Science, vol. 155, Issues 1-2, Aug. 10, 2011.
(Continued)

*Primary Examiner* — Mark Remaly
(74) *Attorney, Agent, or Firm* — K&L Gates LLP

(57) ABSTRACT

The Energy Field and Target Correlation System automatically correlates the characteristics of target particles and a living organism to compute the characteristics of an energy field that is applied to a living organism to activate the target particles which are bound to or consumed or taken up by invasive agents in the living organism to produce detectable effects which can be used to treat the invasive agents. The energy field must be crafted to properly control the response and localize the extent of the illumination. The System automatically selects a set of energy field characteristics, including: field type, frequency, field strength, duration, field modulation, repetition frequency, beam size, and focal point. The determined energy field characteristics then are used to activate field generators to generate the desired energy field.

9 Claims, 13 Drawing Sheets

(51) Int. Cl.
*A61B 18/04* (2006.01)
*A61N 2/02* (2006.01)
*A61B 5/00* (2006.01)

(52) U.S. Cl.
CPC .............. *A61N 2/02* (2013.01); *A61B 5/0059* (2013.01); *A61B 5/0515* (2013.01)

(56) References Cited

U.S. PATENT DOCUMENTS

| | | |
|---|---|---|
| 5,621,188 A | 4/1997 | Lee et al. |
| 6,149,576 A | 11/2000 | Gray et al. |
| 6,165,440 A | 12/2000 | Esenaliev |
| 6,238,421 B1 | 5/2001 | Gunther et al. |
| 6,423,056 B1 | 7/2002 | Ishikawa et al. |
| 6,530,994 B1 | 3/2003 | West et al. |
| 6,961,620 B2 | 11/2005 | Rioux et al. |
| 6,997,863 B2 | 2/2006 | Handy et al. |
| 7,133,725 B2 | 11/2006 | Stirbl et al. |
| 7,174,217 B2 | 2/2007 | Rioux et al. |
| 7,623,908 B2 | 11/2009 | Boppart et al. |
| 7,691,285 B2 | 4/2010 | Teller et al. |
| 7,819,835 B2 | 10/2010 | Landy et al. |
| 7,842,281 B2 | 11/2010 | Haik et al. |
| 7,951,061 B2 | 5/2011 | Foreman et al. |
| 2001/0012912 A1 | 8/2001 | Feucht |
| 2002/0091377 A1 | 7/2002 | Anderson et al. |
| 2002/0193784 A1 | 12/2002 | McHale et al. |
| 2003/0032995 A1 | 2/2003 | Handy et al. |
| 2004/0236278 A1 | 11/2004 | Herweck et al. |
| 2005/0015049 A1 | 1/2005 | Rioux et al. |
| 2005/0059852 A1 | 3/2005 | Rioux et al. |
| 2005/0090732 A1 | 4/2005 | Ivkov et al. |
| 2005/0171433 A1 | 8/2005 | Boppart et al. |
| 2005/0215988 A1 | 9/2005 | Altshuler et al. |
| 2005/0249817 A1 | 11/2005 | Haik et al. |
| 2005/0271745 A1 | 12/2005 | Gruettner et al. |
| 2006/0015098 A1 | 1/2006 | Rioux et al. |
| 2006/0142748 A1 | 6/2006 | Foreman et al. |
| 2006/0163526 A1 | 7/2006 | Teller et al. |
| 2006/0269612 A1 | 11/2006 | Xiang et al. |
| 2007/0010702 A1 | 1/2007 | Wang et al. |
| 2007/0135373 A1 | 6/2007 | Li et al. |
| 2007/0258889 A1 | 11/2007 | Douglas et al. |
| 2008/0103355 A1 | 5/2008 | Boyden et al. |
| 2008/0114429 A1 | 5/2008 | Nagano et al. |
| 2008/0300571 A1 | 12/2008 | LePivert |
| 2008/0319375 A1 | 12/2008 | Hardy |
| 2009/0043256 A1 | 2/2009 | Landy et al. |
| 2009/0054722 A1 | 2/2009 | Sugano et al. |
| 2009/0076496 A1 | 3/2009 | Azure |
| 2009/0076502 A1 | 3/2009 | Azure et al. |
| 2009/0157069 A1 | 6/2009 | Tom et al. |
| 2009/0220968 A1 | 9/2009 | Issadore et al. |
| 2009/0276017 A1* | 11/2009 | Achenbach ............ A61B 18/04 607/100 |
| 2009/0287036 A1 | 11/2009 | Shapiro et al. |
| 2010/0016783 A1 | 1/2010 | Bourke, Jr. et al. |
| 2010/0052668 A1 | 3/2010 | Gleich et al. |
| 2010/0056643 A1 | 3/2010 | Bachynsky et al. |
| 2010/0099941 A1 | 4/2010 | Haik et al. |
| 2010/0160483 A1 | 6/2010 | Vogt et al. |
| 2010/0204674 A1 | 8/2010 | Forbes et al. |
| 2010/0222774 A1 | 9/2010 | Hegg et al. |
| 2010/0292564 A1 | 11/2010 | Cantillon Murphy |
| 2010/0310636 A1 | 12/2010 | Sharma et al. |
| 2011/0104305 A1 | 5/2011 | Day et al. |
| 2011/0125232 A1 | 5/2011 | Landy et al. |
| 2011/0137230 A1 | 6/2011 | Altshuler et al. |
| 2011/0177153 A1 | 7/2011 | Zhu |
| 2012/0065492 A1 | 3/2012 | Gertner et al. |
| 2012/0203050 A1 | 8/2012 | Levy et al. |
| 2012/0259154 A1 | 10/2012 | Hong et al. |
| 2013/0053619 A1 | 2/2013 | McKenna et al. |
| 2013/0053620 A1 | 2/2013 | Susedik et al. |
| 2013/0211249 A1 | 8/2013 | Barnett et al. |

FOREIGN PATENT DOCUMENTS

| | | |
|---|---|---|
| CN | 102008782 | 4/2011 |
| JP | 04-276263 A | 10/1992 |
| JP | 04-348765 A | 12/1992 |
| JP | 05-245217 A | 9/1993 |
| JP | 07-213507 A | 8/1995 |
| JP | 2005-523736 A | 8/2005 |
| JP | 2007500060 A | 1/2007 |
| JP | 2007521109 A | 8/2007 |
| JP | 2010-512910 A | 4/2010 |
| JP | 2011-032238 A | 2/2011 |
| WO | 03/022360 A3 | 3/2003 |
| WO | 2004033038 A2 | 4/2004 |
| WO | 2004105833 A2 | 12/2004 |
| WO | 2005044365 A2 | 5/2005 |
| WO | 2010/139386 | 12/2010 |

OTHER PUBLICATIONS

Barnes et al., *Bioengineering and Biophysical Aspects of Electromagnetic Fields*, Third Edition, 2007, pp. 298 and 299.

Giustini et al., "Magnetic Nanoparticle Hyperthermia in Cancer Treatment," Nano Life, Mar. 2010.

Vertegel et al., "Silica Nanoparticle Size Influences the Structure and Enzymatic Activity of Adsorbed Lysozyme," Langmuir, 2004, 20:6800-6807.

Wikipedia: Physics of magnetic resonance imaging (2014). Retrieved on Aug. 5, 2014 from http://en.wikipedia.org/wiki/Physics_of_magnetic_resonance_imaging.

International Search Report in corresponding PCT Application No. PCT/US11/68114 dated Apr. 19, 2012, 3 pages.

International Search Report in corresponding PCT Application No. PCT/US11/68116 dated May 8, 2012, 3 pages.

International Search Report in corresponding PCT Application No. PCT/US11/68134 dated May 8, 2012, 3 pages.

International Search Report in corresponding PCT Application No. PCT/US11/68142 dated May 4, 2012, 3 pages.

International Search Report in corresponding PCT Application No. PCT/US11/68146 dated May 2, 2012, 3 pages.

International Search Report in corresponding PCT Application No. PCT/US11/68154 dated May 3, 2012, 3 pages.

International Search Report in corresponding PCT Application No. PCT/US12/51763 dated Oct. 22, 2012, 3 pages.

International Search Report in corresponding PCT Application No. PCT/US12/51765 dated Oct. 22, 2012, 3 pages.

PCT Written Opinion of International Searching Authority for International Patent Application No. PCT/US2012/051763, dated Oct. 22, 2012, 6 pages.

PCT Written Opinion of International Searching Authority for International Patent Application No. PCT/US2012/051765, dated Oct. 22, 2012, 6 pages.

U.S. Appl. No. 13/012,527 Non-Final Office Action dated Apr. 29, 2013, 13 pages.

U.S. Appl. No. 13/012,560 Non-Final Office Action dated Apr. 25, 2013, 9 pages.

U.S. Appl. No. 13/012,572 Non-Final Office Action dated May 23, 2013, 12 pages.

* cited by examiner

TARGET PARTICLE DATABASE

| Model | Geometry | Material | Dimensions | Coating | Concentration | Excitation | Response | Function | | |
|---|---|---|---|---|---|---|---|---|---|---|
| | | | | | | Frequency | Field | Phase | Polarization | Field |
| 4756A | Sphere | PEG | 20 nm | None | 50 pico grms/cell | Graph A | 1000 V/m | None | Circular | EM |
| 2377V | Bar | ZincOxide | 5X20X50 nm | Antigen | 70 pico grms/cell | Graph B | 1500 V/m | Horizontal | Vertical | E, EM |
| 9736C | Cylinder | IronOxide | 10X75 nm | PEG | 85 pico grms/cell | Graph C | 1000 V/m, 15000 A/m | Vertical | Horizontal | EM, H |
| 6754Z | Ellipse | PEG Shell, Surfactant filling | 75X45 | Antigen | 65 pico grms/cell | Graph D | 2000 V/m | None | Circular | E, EM |

Figure 3

| Cancer | Nano-Particle Type | Detection Characteristics | Treatment Characteristics | |
|---|---|---|---|---|
| | | | | |
| | 4756A | Material, Thermal | Thermal | |
| BREAST | 2377V | Material | Thermal | |
| | 9736C | Material | Thermal | |
| | 6754Z | Thermal | Thermal | |
| | 4756A | Material, Thermal | Thermal | |
| LUNG | 2377V | Material | Thermal | |
| | 9736C | Material | Thermal | |
| | 6754Z | Thermal | Thermal | |

Figure 4

| Patient | Age | Sex | Weight | Other |
|---|---|---|---|---|
| RG | 56 | F | 178 | Mastectomy |
| AS | 62 | F | 166 | Diabetic |
| FG | 54 | M | 162 | Angioplasty |
| LL | 67 | F | 145 | Diabetic |
| KI | 66 | F | 150 | none |
| | | | | |
| | | | | |

Figure 5

Depth of Penetration - in cm – E, EM Fields Only

| Freq (MHz) | Tissue | | | | |
|---|---|---|---|---|---|
| | Saline | Blood | Muscle (Skin) | Lung | Fat (Bone) |
| 433 | 2.8 | 3.7 | 3.0 | 4.7 | 16.3 |
| 915 | 2.5 | 3.0 | 2.5 | 4.5 | 12.8 |
| 2,450 | 1.3 | 1.9 | 1.7 | 2.3 | 7.9 |
| 5,800 | 0.7 | 0.7 | 0.8 | 0.7 | 4.7 |
| 10,000 | 0.2 | 0.3 | 0.3 | 0.3 | 2.5 |

Figure 7

Reflection Coefficient (in %) between Biological Tissues at 37 deg C E, EM Fields Only

| Material | Freq (MHz) | Fat (Bone) | Lung | Muscle (Skin) | Blood | Saline |
|---|---|---|---|---|---|---|
| Air | 433 | 46 | 76 | 82 | 81 | 83 |
| | 915 | 43 | 73 | 78 | 79 | 80 |
| | 2,450 | 41 | 71 | 76 | 77 | 79 |
| | 5,800 | 39 | 70 | 75 | 76 | 78 |
| | 10,000 | 37 | 70 | 74 | 76 | 78 |
| Fat (Bone) | 433 | - | 46 | 56 | 56 | 60 |
| | 915 | - | 43 | 52 | 54 | 57 |
| | 2,450 | - | 42 | 50 | 53 | 57 |
| | 5,800 | - | 42 | 50 | 53 | 56 |
| | 10,000 | - | 45 | 52 | 54 | 58 |
| Lung | 433 | | - | 14 | 13 | 19 |
| | 915 | | - | 12 | 14 | 18 |
| | 2,450 | | - | 10 | 15 | 19 |
| | 5,800 | | - | 10 | 14 | 19 |
| | 10,000 | | - | 10 | 13 | 18 |
| Muscle (Skin) | 433 | | | - | 4 | 6 |
| | 915 | | | - | 4 | 7 |
| | 2,450 | | | - | 5 | 10 |
| | 5,800 | | | - | 4 | 9 |
| | 10,000 | | | - | 3 | 9 |
| Blood | 433 | | | | - | 6 |
| | 915 | | | | - | 4 |
| | 2,450 | | | | - | 5 |
| | 5,800 | | | | - | 5 |
| | 10,000 | | | | - | 6 |

Figure 6

SYSTEM FOR AUTOMATICALLY AMENDING ENERGY FIELD CHARACTERISTICS IN THE APPLICATION OF AN ENERGY FIELD TO A LIVING ORGANISM FOR TREATMENT OF INVASIVE AGENTS

CROSS-REFERENCE TO RELATED APPLICATIONS

This application is a continuation of and claims priority to U.S. patent application Ser. No. 13/012,539 filed on Jan. 24, 2011, the entire contents of which are incorporated by reference.

FIELD OF THE INVENTION

The invention relates generally to the field of treatment of invasive agents, such as pathogens and cancers, in living organisms and, more particularly, to a system that matches input energy field characteristics, as applied to the living organism, with the characteristics of particles which are infused into the living tissue that is to be imaged, or treated, or imaged and treated.

BACKGROUND OF THE INVENTION

It is a problem to accurately detect the presence of and determine the locus of invasive agents, such as pathogens and cancers (malignant neoplasm), (collectively termed "invasive agents" herein) in a living organism (ex.—human, animal). Most invasive agents are initially recognized either because signs or symptoms appear in the living organism that is infected with the invasive agents or through screening tests which commonly include blood tests, X-rays, CT scans, MRI and endoscopy, for example. None of these processes leads to a definitive diagnosis, which usually requires the opinion of a pathologist who specializes in the diagnosis of invasive agents and other diseases. However, even with expert analysis, the diagnosis is still somewhat subjective in nature.

Presently, a procedure is being used where nano-particles are directed to invasive cells (cancer cells) by the use of passive and active targeting methods. The passive targeting approach uses the size and shape of the nano-particles to enhance their uptake into cancer cells while the active targeting approach uses coatings applied to the nano-particles (such as an antigen) to enable the targeted uptake of the nano-particles by only those cells, cancer cells for instance, that are susceptible to the antigen coating. Other coating methods using other materials are presently being studied by those in the art to facilitate nano-particle uptake in cancer cells.

Now that nano-particles can be inserted into the living organism through intravenous application as well as direct injection of particles at the cancerous site, and uniquely directed to specific cancer cells via either active or passive targeting, an opportunity exists for enhanced imaging of cancerous lesions. Conceptually, since many thousands of nano-particles can fit into a cancer cell, non-lumpy cancers could be "imaged" or detected. This is a function of using the correct frequencies and energy levels to enable imaging at the desired size or scale resolution. In concept then, mammograms for breast cancer imaging, which have size resolution detections in the tens of millimeters range, would be clearly eclipsed by the approaches described herein which can conceptually image at the cellular level.

Recent laboratory techniques have been explored using nano-particles as a contrast agent, seeking to improve both the imaged Signal-to-Noise ratio as well as the differentiation between cancerous tissue and healthy tissue, provided that the nano-particles were targeted to the cancer cells. Some of these published techniques have discussed using the notion of micro-bubbles, thereby creating an air dielectric region. This technique is easily replicated in the lab but does not readily translate to the in vivo live human environment. Other techniques have used iron ferrite particles, but with limited contrast improvement. What is needed is a nano-particle/field pairing that optimizes the "output energy" response of the nano-particles to enable enhanced imaging over what is accomplished in today's art.

One such possible imaging method involves the use of an acoustic imaging system. Tissue responds to an energy pulse, whether it is RF or microwave or laser, by expanding under the influence of the energy pulse, and then contracting. During such physical changes, albeit extremely slight, the tissue emits an acoustical signature that is unique to its material composition. Similarly, a specially designed particle that responds, preferably dramatically, to the EM or laser energy pulse, would create a significant and correlated acoustic response. This is one method of enhanced imaging detection, by using nano-particles that are specially designed to emit an enhanced acoustical signature when illuminated, where the acoustical signature is unique to the nano-particle and different from the surrounding tissue response.

Alternatively, a second possible imaging method involves directly using the material properties of the nano-particles to enhance imaging contrast. Nano-particles can be designed and made in significant volume with consistent material properties which are unique and novel compared to normal tissue, say breast tissue. However, the efforts to date using nano-particle material properties have involved using traditional MRI contrast agents but in a non-MRI environment. Again, this is non-optimal and results in a method that does not fully exploit the notion of pairing nano-particle with field types to maximize imaging capabilities. If the illuminating field types were matched to the material properties of the nano-particle, the nano-particle can be detected by the very nature of their material properties, where the properties are uniquely different from that of normal tissue, and an advance would be made that is unique and novel over the existing art.

Using cancer as an example, there are presently several common approaches to treating cancer, once it is detected: surgical, chemotherapy, radiation therapy, immunotherapy, and monoclonal antibody therapy, all of which have severe negative effects on the living organism. A significant problem with this paradigm is that the diagnosis and treatment of invasive agents are radically different processes with limited linkage between the two.

The surgical approach to cancer treatment is the traditional process where a surgeon makes an incision into the living organism and manually attempts to excise the cancerous tissue. A problem with this approach is that it is invasive, stressful to the living organism, and difficult to precisely excise only the cancerous tissue and not remove healthy tissue from the site of the cancer. While removal of small amounts of healthy tissue is typically not problematic, it is difficult to excise all the cancerous tissue, with minimal healthy tissue and not leave behind any cancerous tissue. Therefore the typical surgical practice is to remove a "reasonable" amount of surrounding healthy tissue, since the downside of missing cancerous cells is unacceptable recurrence of the cancer. The surgical approach is therefore traumatic and imprecise.

Chemotherapy is the use of toxic chemicals (drugs) to kill the cancer cells. This procedure typically results in severe side effects since the chemotherapy drugs also negatively impact the living organism, killing healthy cells, injuring the vital organs in the process of destroying the cancerous cells. A long regimen of chemotherapy is required to cleanse the living organism of the cancer cells and in many cases a combination of drugs is used to ensure that the cancer cells are destroyed. Most commonly, chemotherapy acts by killing cells that divide rapidly, one of the main properties of most cancer cells. This means that it also harms cells that divide rapidly under normal circumstances: cells in the bone marrow, digestive tract and hair follicles; this results in the most common side effects of chemotherapy—myelosuppression (decreased production of blood cells), mucositis (inflammation of the lining of the digestive tract) and alopecia (hair loss). Newer anticancer drugs act directly against abnormal proteins in cancer cells; this is termed targeted therapy. An additional problem with chemotherapy is that the cancer cells adapt to the treatment, developing immunity to the drugs that are administered, thereby requiring a sequence of different drugs to provide an effective treatment.

Radiation Therapy is the use of radiation to kill the cancer cells. This procedure typically results in severe side effects since the radiation also negatively impacts the living organism, killing healthy cells as well as the cancerous cells. A long regimen of radiation therapy is required to cleanse the living organism of the cancer to ensure that the cancer cells are destroyed. Radiation therapy is the medical use of ionizing radiation as part of cancer treatment to control malignant cells and may be used for curative or adjuvant treatment. It is also used as palliative treatment (where cure is not possible and the aim is for local disease control or symptomatic relief) or as therapeutic treatment (where the therapy has survival benefit and it can be curative). It is also common to combine radiotherapy with surgery, chemotherapy, hormone therapy or some mixture of the three. Most common cancer types can be treated with radiation therapy in some way. The precise treatment intent (curative, adjuvant, neoadjuvant, therapeutic, or palliative) depends on the tumor type, location, and stage, as well as the general health of the subject.

Radiation therapy is commonly applied to the cancerous tumor. The radiation fields may also include the draining lymph nodes if they are clinically or radiologically involved with tumor, or if there is thought to be a risk of subclinical malignant spread. It is necessary to include a margin of normal tissue around the tumor to allow for uncertainties in daily set-up and internal tumor motion. These uncertainties can be caused by internal movement (for example, respiration and bladder filling) and movement of external skin marks relative to the tumor position. To spare normal tissues (such as skin or organs which radiation must pass through in order to treat the tumor), shaped radiation beams are aimed from several angles of exposure to intersect at the tumor, providing a much larger absorbed dose there than in the surrounding, healthy tissue. Radiation therapy works by damaging the DNA of cells. The damage is caused by a photon, electron, proton, neutron, or ion beam directly or indirectly ionizing the atoms which make up the DNA chain. Indirect ionization happens as a result of the ionization of water, forming free radicals, notably hydroxyl radicals, which then damage the DNA. In the most common forms of radiation therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly.

Cancer immunotherapy attempts to stimulate the immune system to reject and destroy tumors. In the beginning immunotherapy treatments involved administration of cytokines such as Interleukin with an aim of inducing the lymphocytes to carry on their activity of destroying the tumor cells. Thereafter, the adverse effects of such intravenously administered cytokines lead to the extraction of the lymphocytes from the blood and culture-expanding them in the lab and then injecting the cells alone to enable them to destroy the cancer cells.

Monoclonal antibody therapy is the use of monoclonal antibodies (or mAb) to specifically bind to target cells. This may then stimulate the patient's immune system to attack those cells. It is possible to create a monoclonal antibodies specific to almost any extracellular/cell surface target; thus, there is a large amount of research and development to create monoclonal antibodies for numerous serious diseases (such as rheumatoid arthritis, multiple sclerosis and different types of cancers). There are a number of ways that monoclonal antibodies can be used for therapy. For example: monoclonal antibodies therapy can be used to destroy malignant tumor cells and prevent tumor growth by blocking specific cell receptors.

A new, relatively imprecise approach to diagnose cancer is the injection of nano-particles into the living organism and the subsequent activation of the nano-particles via the use of a magnetic field. The size of the nano-particles is selected to enable the cancer cells to ingest the nano-particles, yet not be able to excrete the ingested nano-particles. In addition, the nano-particles can be coated with a substance to make the nano-particles more susceptible to ingestion by the cancer cells, or more likely to bind to the cell surface of the cancer cells. The nano-particles can be heated to raise the temperature of the cancer cells, thereby killing the cancer cells, or the nano-particles can be formed to encapsulate cancer-killing drugs, which are released into the cancer cell by the application of the magnetic field. However, this process is in the early stages of development and has yet to reach a level of maturity where the physical processes and their limitations are well understood.

Thus, there presently is no procedure that can be used to accurately detect the presence of cancer cells in a living organism or treat the cancer cells, once detected, to destroy the cancer cells, without serious negative effects on the living organism. Present diagnostic and treatment procedures are macro and non-specific in their approach and result in damage to the living organism in order to destroy the cancer cells. Additionally, the cost of present day imaging methods, such as an MRI or CT scan, is prohibitive for annual screening check-ups and is reserved for only the most serious of cases. Routine mammograms, specialized x-rays of the human breast, offer limited contrast as well as limited resolution. Mammogram resolution is only to the tens of millimeters range, and some mammograms cannot detect physical masses less than five millimeters. In addition, mammograms have a very high false positive rate, meaning subsequent additional tests are necessary just to "make sure". Worse yet, mammograms often fail to find true cancerous lesions. Certain tissue types, such as fibrous breasts, common in older women, and breast implants made of saline and other materials, further complicate the accuracy of mammograms. Finally, mammograms use an ionizing method of imaging that over time is additive and harmful to healthy tissue. What is needed is a low cost, ubiquitous, non-ionizing imaging method wherein breast imaging enhancement can be realized via the unique pairing of non-ionizing illuminating fields with nano-particles of specific material properties, where the nano-particle response, in the given illuminating field, enables an enhanced signal to noise ratio and higher contrast than current imaging methods.

BRIEF SUMMARY OF THE INVENTION

The above-described problems are solved and a technical advance achieved by the present System For Automatically Amending Energy Field Characteristics In The Application Of An Energy Field To A Living Organism For Treatment Of Invasive Agents (termed "Energy Field and Target Correlation System" herein) which automatically produces a correlation between the characteristics of target particles which are deployed in a living organism and an energy field that is applied to the living organism to activate the target particles to produce detectable effects which can be used to image, treat, or image and treat an invasive agent located in the living organism. The use of target particles is necessary to create a differentiation in the effect created by the illumination of a target area of the living organism in which the invasive agent is present between normal cells in the living organism and the invasive agents found in the living organism, which differentiation is accomplished by the contrast produced by the activated target particles. By the precise generation of the energy fields as a function of characteristics of the target particles, living organism and invasive agent, a specific well-defined response to the illumination of the target particles is produced and unambiguously detected to accurately produce the effects of the treatment of the invasive agent. This response is then mapped using detection and signal processing methods, where the output energy is of an acoustic or backscatter nature, thereby realizing a significant advance in terms of both signal to noise ratio and contrast with normal tissue. The measured response can be used to amend the generated energy fields in order to precisely control the treatment process. This virtually ensures that cancers are treated at very early stages, whether it is breast cancer or some other type of cancer, where it is then significantly easier to treat and kill the invading cancer. This is true for lumpy cancers as well as metastatic cancers, including blood-borne cancers.

The following description uses cancer as an example of an invasive agent, since much research has been done in this field and the diversity of cancers that are found in a living organism is extensive. The automatic mapping of the energy field characteristics to the characteristics of the target particles, such as nano-particles, is critical to enable a determination of the presence of the cancer cells and the precise location of the cancer cells as well as the treatment of the cancer cells. Of note, while the methods and techniques described herein focus on breast cancer detection, the technology is applicable to any type of biological invasive agent such as HIV or even the common cold. Other diseases may be imaged using these methods by attaching a nano-particle to a molecule, say a molecule which shows or predicts Alzheimer's, and then the extent of that protein could be imaged. Nerves could be mapped using these approaches where today nerves are difficult if not impossible to see using contemporary imaging methods. Nano-particles can be made to attach to DNA strands of specific type—these DNA strands could then be imaged and mapped. In short, since nano-particles are as small as the smallest of biological structures, these techniques are not limited to just cancer and imaging cancer cells physical extent; but rather, the methods described herein could be used to detect and treat virtually any type of invasive agent or non-normal biological material, behavior, mechanism or process.

Note that the locus of the cancer cells may be dynamic, such as in the case of a blood-borne cancer. In this example, the movement of the cancer cells within the bloodstream creates an added complexity to the treatment process. In cancers that are in the process of metastasizing, the blood system and the lymph system create pathways for the cancer to spread to other loci. Thus, there is a time domain component in conjunction with a spatial domain component. For most cancers, and breast cancer in particular, the time domain component can often be ignored and just the spatial domain component is of interest.

The target particles are activated by a precisely crafted energy field, as manually or automatically selected by the Energy Field and Target Correlation System, to provide illumination of the target particles with the minimum required energy to create the selected effects. In addition, the mapping of characteristics provides great flexibility and enables the concurrent use of multiple types of target particles. Since there is a great diversity in cancer cells, there must be a corresponding diversity in the target particles which are designed to be implanted in the specific cancer cells and responsive to the applied energy fields. Furthermore, the site of the cancer can vary in terms of depth within the living organism and this has significant implications in terms of the strength and focus of the energy fields, since each interface in the living organism encountered by the incident energy field(s) can cause dissipation, diffraction and reflection of the incident energy field(s). Also each living organism has characteristics that define the illumination environment and limitations on the type and duration of the energy fields that are used.

Certain energy field types, such as a magnetic field, are less susceptible to tissue interaction as the field propagates into the in vivo body to the nano-particle locus. However, if the magnetic field construct of field strength multiplied by the excitation frequency is too high, eddy currents can be induced in the body or in the tissue, which can cause unintended heating. There is a balancing of illumination attributes that must be considered. While a magnetic field has less tissue artifacts to deal with, a magnetic field cannot be used when metallic objects are embedded in the body, such as pace makers, orthopedic screws/pins and so on. An electric or electromagnetic field may be better suited for situations where metallic objects are present since it may be easier to highly target the illumination to just the area of interest versus a large macro region of the body.

Thus, the Energy Field and Target Correlation System automatically selects a set of energy field characteristics, from the characteristics of energy fields including field type, frequency, field strength, duration, field modulation, repetition frequency, beam size and focal point, that is required to energize the target particles in a selected manner in the portion of the target living organism that is being analyzed. The determined energy field characteristics are then used to activate one or more energy field generators to generate an energy field having the selected energy field characteristics for application to the portion of the target living organism to treat invasive agents in the living organism.

It is important to note that the activation of nano-particles by the Energy Field and Target Correlation System is highly deterministic, meaning that a given particle is optimally activated or excited by a given energy field of pre-defined characteristics. Generic or random field excitations do not optimally excite a given particle. The field excitation of a nano-particle is considered to be the "input energy" or "input driving function" of the system. In general, the "input energy" is converted by the nano-particles to an "output energy" which is then detected by means described herein. It is this "output energy" which is first detected, and then, using signal processing methods, used to formulate an image of the breast tissue, for example. Thus, the Energy Field and Target Correlation System has an input energy function that is used to activate nano-particles, which in turn respond with an "output energy function" which is unique to that nano-particle.

While we have discussed the notion of active imaging by placing nano-particles in diseased or cancerous tissue, there is nothing to prevent the converse, that is, to place nano-particles into healthy cells and image only those cells. Then the absence of imaged space would identify a region of material that is not biologically healthy and, therefore, assumed to be cancerous. Alternatively, two nano-particle IVs or injections (or both) could be given, one nano-particle designed to be taken up by diseased or cancerous cells, the other for healthy cells. This creates an extreme level of contrast between the two types of nano-particles. Another approach is to use as many unique nano-particle types as is needed to identify the many cancerous or un-healthy cellular types present in the living organism. Then, the imaging process would identify those cancers, as they relate to each other, in full spatial extent. To further enhance this imaging separation, different energy fields (E, H, EM, acoustic, optical) could be used for each nano-particle type to ensure full isolation between the "input energy function" and the "output energy function". The excitation of the different nano-particle types could also be managed in the time domain, where the nano-particles are successively illuminated by their respective paired energy fields. Thus, there are many degrees of freedom present in the Energy Field and Target Correlation System, where the degrees of imaging freedom enable an optimal imaging environment.

The following description provides a brief disclosure of these elements of the System in sufficient detail to understand the teachings and benefits of the Energy Field and Target Correlation System. It is expected that many other applications of the System can be envisioned by one of ordinary skill in the art, and the Energy Field and Target Correlation System is simply one application of an invasive agent treatment system, which is delimited by the appended claims.

BRIEF DESCRIPTION OF THE DRAWINGS

FIG. 3 is an example, in table format, of target particle characteristics for nano-particles;

FIG. 4 is an example, in table format, of a cancer to target particle effect mapping for a plurality of target particles;

FIG. 5 is an example, in table format, of a patient characteristics database;

FIG. 6 illustrates a table of data that characterizes the reflection coefficient that occurs at the junction between various types of biological tissue types;

FIG. 7 illustrates a table of data that characterizes the depth of penetration of an electromagnetic wave in different tissue types as a function of frequency of the electromagnetic wave;

DETAILED DESCRIPTION OF THE INVENTION

Figure 1A:
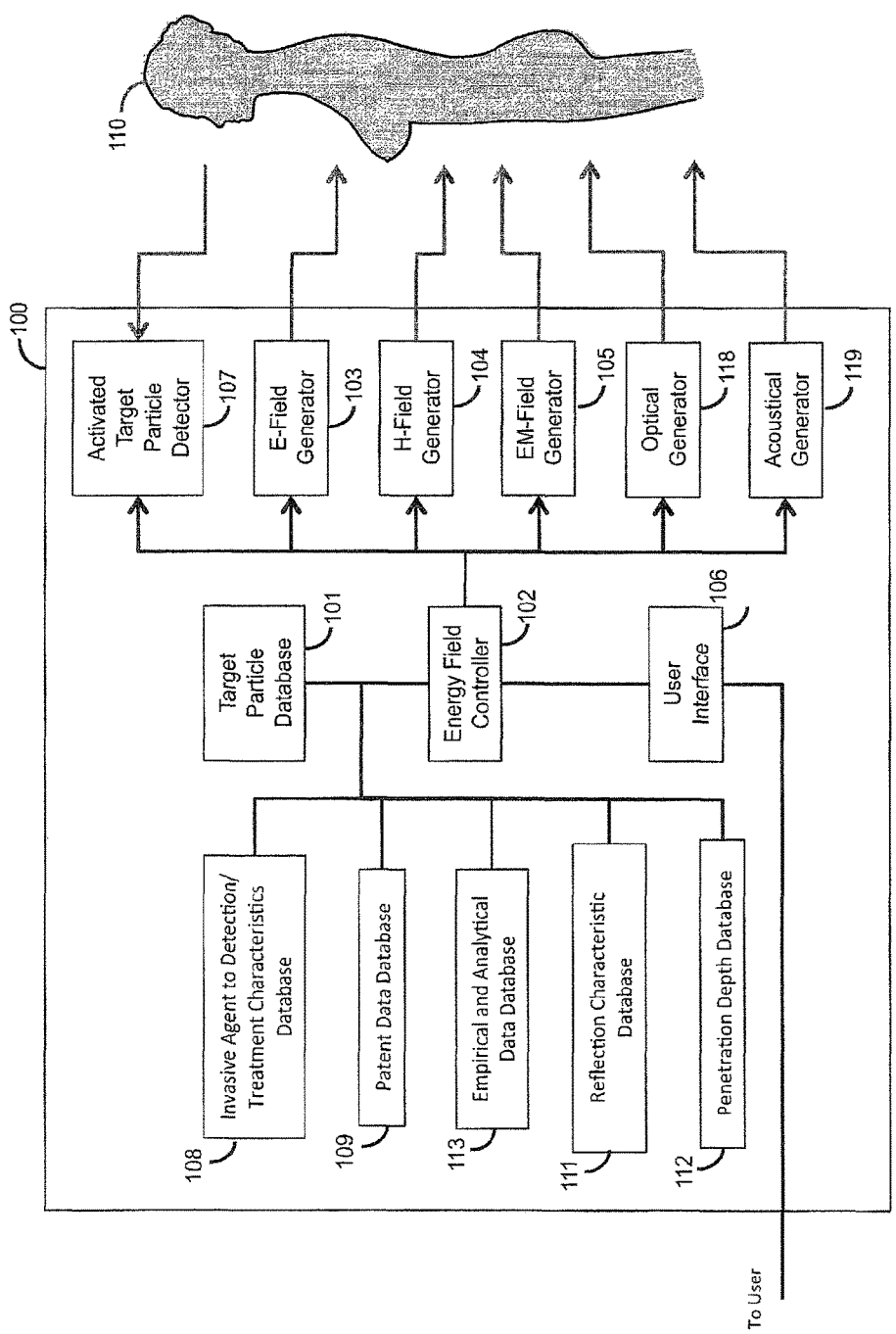
FIG. 1A illustrates, in block diagram form, the typical architecture Energy Field and Target Correlation System.

The use of target particles is necessary to improve differentiation between normal cells in the living organism and the invasive agents found in the living organism, which differentiation is accomplished by the contrast produced by the detectable effects of activated target particles. The Energy Field and Target Correlation System is directed to the application of an energy field (electric, magnetic, both) to a living organism (typically human or animal) to activate target particles which have been deployed in the living organism, which target particles bind to the invasive agents or are taken up by the invasive agents. The activation fields can take on the following forms: an E-field, an H-field, an EM-field, optical fields such as lasers, acoustic fields, and so on. The target particles can exhibit a response that is thermal, mechanical, electric, or chemical in nature, as a function of the characteristics of the target particles. This response of the target particles to the energy field represents detectable phenomena that pinpoint the invasive agents to which the target particles are either bound or taken up. The target particles can reside in the cellular regions of the invasive agent or they could reside in the region of the healthy cellular tissue or both. In the case where both regions are mapped with nano-particles, the nano-particles would exhibit a unique response thereby enabling a differentiation between the two regions. Different invasive regions could have different nano-particles, where the nano-particle response enables a differentiation of the different invasive cellular volumetric extents.

The energy field must be coordinated with both the characteristics of the portion of the living organism that is being analyzed together with the characteristics of the target particles, especially in the case where multiple types of target particles are implanted in the living organism, to properly control the response and localize the extent and intensity of the illumination. The Energy Field and Target Correlation System determines the relationship between the invasive agent and the detection/treatment characteristics for a selected type of target particle and the detected invasive agent. Then the Energy Field and Target Correlation System automatically (or in a manual human-derived means for certain situations) selects a set of energy field characteristics, from the characteristics of energy fields including: field type, frequency, field strength, duration, field modulation, repetition frequency, beam size and focal point, that is required to energize the target particles in a selected manner in the portion of the target living organism that is being analyzed. The determined energy field characteristics are then optionally compared to data stored in an empirical and analytical data database which provides access to information indicative of experimental, modeled, or experiential data which can be used to build a set of illumination functions. These illumination functions are used to compute a sequence of energy field controls which activate one or more field generators to generate an energy field having the selected energy field characteristics for application to the portion of the target living organism to treat invasive agents which are located in the living organism.

Each target particle to living organism to invasive agent mapping is unique, to some degree, and this is part of the systems process, to recognize and adapt for this uniqueness or variability to create a custom or semi-custom treatment regimen or protocol. In addition, dynamic feedback is an enhancement which allows the real-time monitoring of the generated effects to determine whether the illumination process needs to be adapted to achieve the desired results. Thus, an area that is being imaged which is not clearly defining its cancer extent boundaries could be re-imaged with new parameters, such as enhanced field strength, to improve boundary resolution. Another form of dynamic feedback could be during a treatment protocol, where the particles being illuminated are sensed for thermal rise, and the illumination function is adjusted to analyze a specific temperature in this cancerous tissue.

Invasive Agents

There are a number of possible invasive agents that can be found in a living organism, and these can include viruses, bacterium, cancers, and the like. An infection is the detrimental colonization of a host organism by a foreign parasite species. Infecting organisms seek to utilize the host resources to multiply, usually at the expense of the host. The immune system of mammalian hosts reacts to infections with an innate response, often involving inflammation, followed by an adaptive response. Colloquially, a pathogen is usually considered a microscopic organism though the definition is broader, including macro parasites, fungi, viruses, prions, bacteria, and viroids. A further class of invasive agents is cancers. Cancer is a class of diseases in which a cell or a group of cells display uncontrolled growth, invasion (intrusion on and destruction of adjacent tissues), and sometimes metastasis. A separate class of agents which are not strictly "invasive" in nature include fat cells, uric acid "crystals", kidney stones, etc. These agents are included in the classification of invasive agents herein for simplicity of description.

Cancer—Malignant Neoplasm

Cancer (medical term: malignant neoplasm) is a class of diseases in which a cell, or a group of cells display uncontrolled growth, invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not. In order to simplify the following description of the present Energy Field and Target Correlation System, cancer is used as an example of an invasive agent which can be detected by the present Energy Field and Target Correlation System.

Use of Target Particles to Detect and Treat Cancer Cells

FIG. 1A illustrates, in block diagram form, the typical architecture Energy Field and Target Correlation System 100 as used with a specific instance of a living organism 110. In operation, the target portion of the living organism 110 is populated with target particles of a predetermined type or types. This population of target particles could be delivered in a variety of fashions to include but not limited to: intravenous delivery, injected delivery, a skin cream and the like. The target particles themselves can take on at least two generic forms of delivery after initial administration: active and passive. Active delivery particles are particles which are selectively taken up by the invasive agent or cancer cells because of a preferred antigen (or other substance) while passive particles use their shape size or physical configuration to be selectively taken up by the cancer cells. Alternatively, it is possible for all cell types, healthy and cancerous, to take up the target particles and the cancer cells, due to their different pH, cause the target particle to change such as "melt" an outer layer off of the target particle because the pH of a cancer cell is typically different to the pH of a healthy cell. In this case, the two target particle types are now different, a modified target particle in the cancer cell and an original target particle in a healthy cell. Thus, in the healthy cell, where the shell did not melt or dissolve, the cytotoxin, for example, would not be released (but it would be released in the cancerous cell).

These target particles are designed to attach to or be absorbed by the cancer cells (invasive agents) of interest to enable detection of the presence and locus of the cancer cells. For the sake of simplicity of description, the target particles used herein as an illustration are nano-particles and these terms are used interchangeably, without intending to limit the scope of target particles that could be used. Some empirical evidence suggests that a higher uptake probability in cancer cells occurs if both IV and injection delivery are utilized simultaneously. The first is via Intravenous (IV) delivery of the target particle solution to the bloodstream. The second is via injecting the target particles directly at the tumor site. Nothing herein precludes any method of delivery of target particles to the cancer site and all delivery methods, whether active or passive, are considered covered by this systems level approach to cancer treatment. Active delivery involves the use of targeting molecules or coatings on the exterior of the target particle that are preferred by cancer cells and rejected by other, healthy cells. Passive delivery uses the unique physical attributes of the target particle, such as length or width, to only be taken up by cancer cells and not by other, healthy cells. It is possible to use both Active and Passive methods in a concurrent fashion as well. Furthermore, healthy cells can uptake nano-particles, either the same as taken up by the cancer cells or other nano-particles specifically targeted to healthy cells. To be clear, the imaging could be accomplished via target particles in cancer cells, or the converse of target particles in healthy cells, or the combination of two different target particles, each residing in their respective cells, cancerous and healthy. Different methods may be used for different patients to identify cancerous or invasive cells. As an example, in a patient that has a very small cancerous mass, where highly enhanced contrast is needed due to the cancer's proximity to major blood vessels, the target particles that are delivered to the cancerous cells could be activated or excited by an E-field while the target particles delivered to healthy cells could be activated or excited by an H-field. Both the E and H excitation could be simultaneously realized via unique fields or via a field that contains both wave types such as an EM-field. Other combinations are clearly possible and nothing herein limits the imagination or vision of the treating physicians to use the most optimal pairing of target particles and fields for a given imaging case. After a sufficient preparation time to enable the target particles to reach their desired destination, the living organism 110 is illuminated by energy fields which are automatically selected and produced by the Energy Field and Target Correlation System 100 to enable the Activated Target Particle Detector 107, which is responsive to activation of the target particles, for producing an interpretable representation of the targeted portion of the living organism 110 to illustrate the presence, locus and response of the activated target particles.

The Activated Target Particle Detector could take on a number of forms. The first form could be an ultra-sonic array that is designed to pick up or receive the emitted acoustical signature of the tissue and target particles when under a pulsed illumination, such as in thermal acoustic or photo acoustic imaging. The second form could be a microwave antenna receiving array that picks up the back scatter or scattering components of the tissue and target particles. These detectors, while not shown in FIG. 1A, would reside at the input to device 107 which is a sub-device of element 100.

In particular, there are a number of databases which maintain information which is relevant to the disclosed or imaging process. In particular, a Target Particle Database 101 maintains a listing of characteristics of at least one type of target particle, from the characteristics of target particles including: size, shape, material composition, surface coating, geometry, contents. The Invasive Agent-To-Detection Characteristics Database 108 maintains data which characterizes the relationship between the invasive agent and the characteristics needed to produce a detectable effect for a selected type of target particle. In addition, Patient Data Database 109 maintains patient-specific data which provides data regarding the age, sex, weight, prior surgeries or other conditions relevant to the treatment process. The Empirical And Analytical Data Database 113 maintains information which has been collected via modeling, testing, theoretical computations, and the like. The Reflection Characteristics Database 111 contains data which represents the percentage of an incident signal which is reflected at the interface between two materials, biological, water, air or the like. Finally, the Penetration Depth Database 112 contains data which represents the attenuation of an incident signal as it passes through a selected material. The number and contents of these databases are selected to illustrate the concepts of the Energy Field and Target Correlation System 100 and are not intended to limit the application of the Energy Field and Target Correlation System 100.

There are also one or more Field Generators 103-105, 118, and 119 for generating an energy field. An Electric Field Generator 103 is shown for producing an electric field; a Magnetic Field Generator 104 is shown for producing a magnetic field; an Electromagnetic Field Generator 105 is shown for producing an electromagnetic field; an Optical Generator 118 is shown for producing NIR, IR Optical, and UV inputs; and an Acoustical Generator 119 is shown for generating sonic and ultrasonic inputs. Any combination of these Field Generators may be present and can be activated individually or simultaneously, as required. At the outputs of each of these field generators, there are illumination radiators which may comprise electric antenna elements, magnetic antenna elements, optical elements, acoustic elements, and/or arrays of these elements. The purpose of these radiators (not shown in FIG. 1A for clarity) is to provide the Output Energy Function or the energy impulse that excites the tissue and the target particles. The radiators could be polarized in any combination of elliptical polarizations including linear or circular. The output energy might consist of either continuous, modulated, or pulsed energy in any frequency band from acoustic through RF and microwave through infrared and optical An Energy Field Controller 102, which is responsive to a user selecting, via the User Interface 106, at least one type of the target particles and identifying a portion of a target living organism which contains these target particles, automatically selects energy field characteristics, from the characteristics of energy fields including: field type, frequency, field strength, duration, field modulation, repetition frequency, beam size and focal point, to energize the selected target particles in a selected manner in the identified portion of the target living organism. Thus, the user inputs data relating to the class of target particles and the portion of the living organism that is being treated, which causes the Energy Field Controller 102 to automatically determine the appropriate set of energy field characteristics, which are required for application to the designated portion of the target living organism to activate the target particles to respond in a detectable manner to enable the identification, via an Activated Target Particle Detector 107, of a presence, locus and response of the target particles in the living organism (as disclosed in further detail below). The Energy Field Controller 102 uses the automatically determined set of energy field characteristics to activate the corresponding Energy Field Generator(s) 103-105, 118, and 119 to output the corresponding energy fields as defined by the set of energy field characteristics. It should be noted that an automated system would help improve accuracy and prevent human imaging errors; but nothing herein prevents this system from being operated in a manual form, should a special case arise wherein a manually entered algorithm could potentially enable higher imaging contrast or resolution; or better, a more efficacious treatment protocol.

Basis for Detection and Treatment of Invasive Agents

One basis for the active detection and treatment of breast cancer sites is the significant contrast in dielectric properties between normal breast tissue and malignant breast tissue at a selected frequency spectrum. At this frequency range, tumors and muscle tissues rich in water content exhibit higher dielectric properties than low water content tissues, such as the fat which forms the major part of normal breast tissue. Since the vast majority of breast tumors originate within fibroglandular breast tissue, the malignant lesion is a weakly scattering target within a high clutter environment. To address this imaging scenario, using dielectric or conducting micro- and/or nano-particles as contrast agents enhances the dielectric-properties contrast between the tumor and surrounding normal fibroglandular tissue. This is shown in FIG. 1B at steps 120, 122, 125, and 126 as material property imaging methods.

Figure 1B:
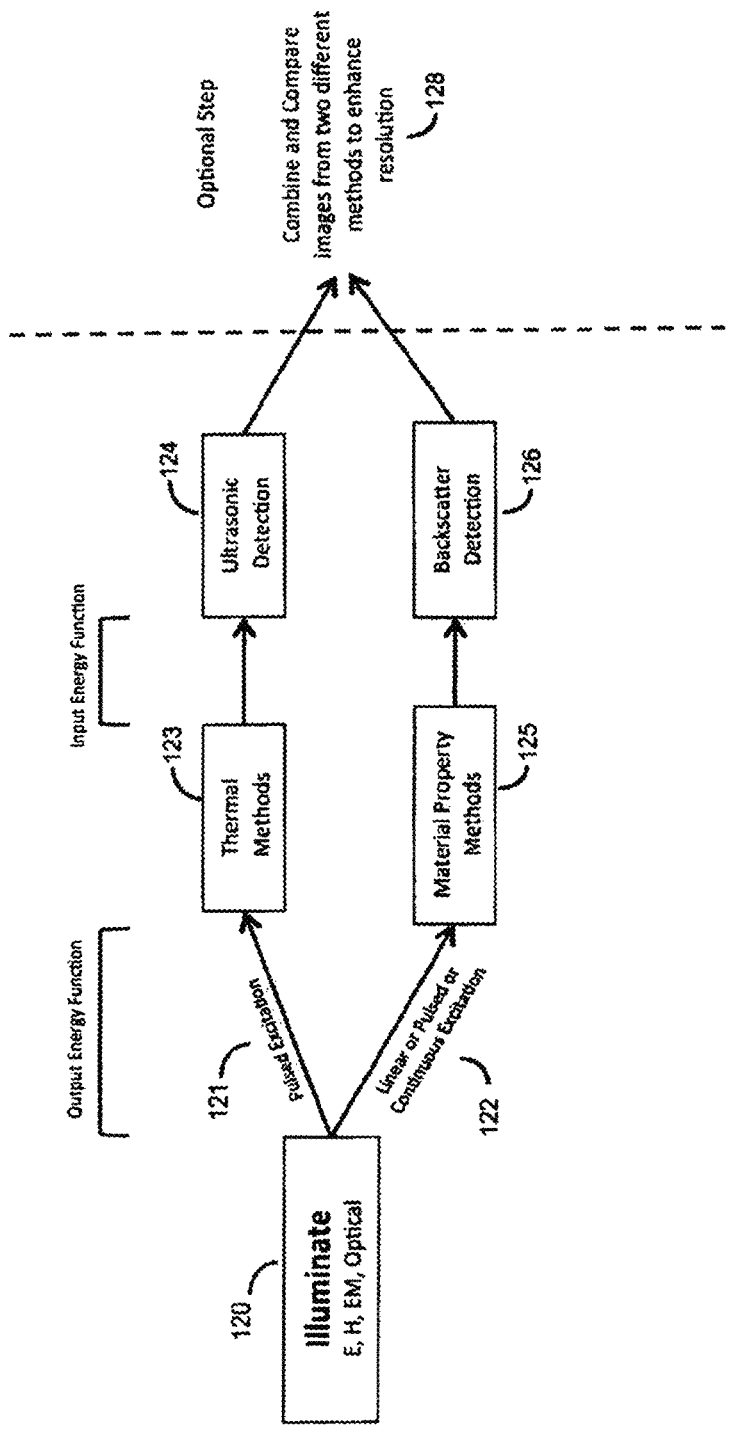
FIG. 1B illustrates two methods of imaging, each having a different "input energy function" used to create different "output energy functions"

FIG. 1B shows the Illumination Function, 120, as it relates to two methods of imaging, Thermal Methods 123 and Material Property Methods 125. This is further described in greater detail in FIG. 1C. For the thermal method, electromagnetic energy, optical, laser, RF or microwave 140, is applied to a tissue sample at step 141 as a pulse of energy 142, where the tissue generates heat at step 146 as a result of the energy pulse and subsequent thermal expansion of the cells at step 148 in the tissue produces an acoustic wave that is measured by an array of acoustic sensors at step 150 (also shown as ultrasonic detection 124 on FIG. 1B). Thermo-acoustic (RF or microwave) and photo-acoustic (optical or laser) imaging, therefore, are inverse source problems, providing completely different contrast mechanisms than traditional diagnostic, imaging techniques. Differential heating in cancerous and noncancerous tissue, for example, can thereby be used to produce an image. However, certain healthy tissue types have acoustical signatures similar to some cancerous tissues, meaning it is often difficult to realize high levels of contrast between cancerous and healthy tissue. The addition of specialized nano-particles greatly enhances the imaging contrast of cancerous tissue. This is of particular importance for breast cancer imaging.

The Thermal Method has a pulsed excitation function (the output of the system is a pulse of energy, optical laser or microwave energy) where both the tissue and the particles exhibit a slight deformation of physical shape resulting in an acoustical signature which is detected and mapped. The acoustic response of nano-particles (target particles) is distinctly different from tissue, thereby adding an element of contrast where tissue types have similar signatures. This also enhances the signal to noise ratio, further enhancing the images realized. Particles can be designed to have an enhanced thermo acoustic response or photo acoustic response.

Figure 1C:
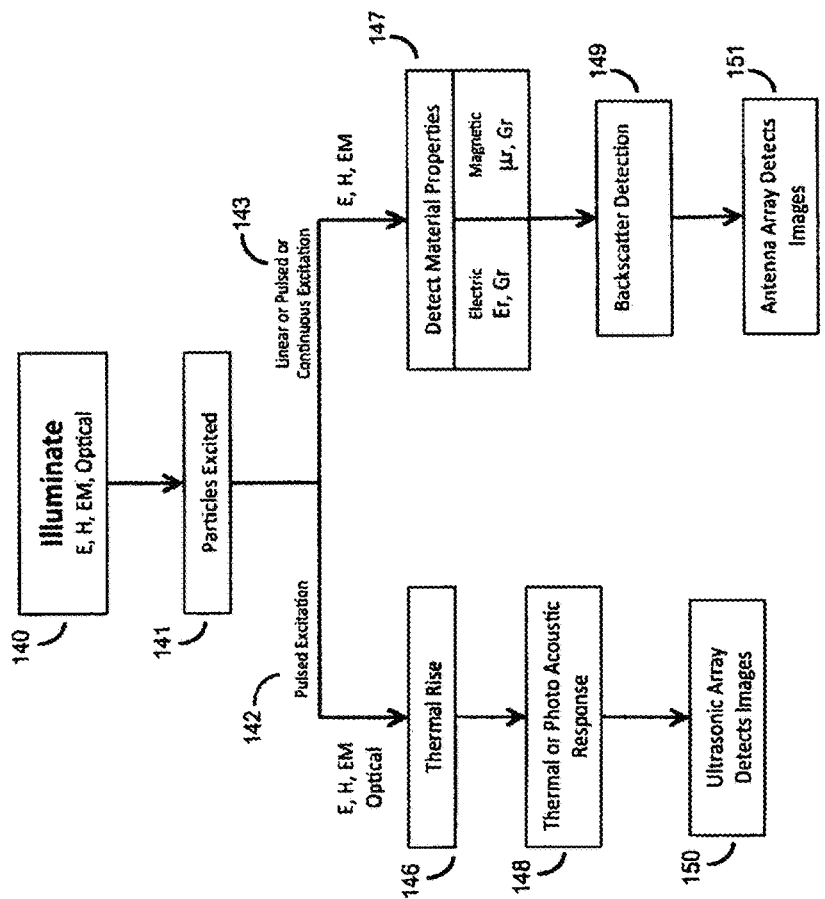
FIG. 1C illustrates the two methods of FIG. 1B in greater detail.

The Material Property Method of detection uses the material properties of the nano-particles to differentiate the backscatter response of different types of tissue. In one implementation, RF or microwave energy (step 140) is applied to a tissue (step 141) as a linear, pulsed, or continuous excitation (step 143). In this implementation, the material properties detection method uses the permittivity ($\epsilon_r$) and conductivity ($\sigma_r$) for E- and EM-Fields (FIG. 1C, step 147) and permeability ($\mu_r$) and conductivity ($\sigma_r$) for an H-Field (FIG. 1C, step 147). This can be accomplished by the direct measured difference in material properties, as detected at steps 126, 149 by backscatter detection, due to the fact that the particles can have materials properties from cancerous and healthy tissue. As an example, tissue does not exhibit a pronounced permeability; therefore nano-particles that have a pronounced permeability would clearly stand out in a magnetic field excitation. Note also that the excitation could be by both fields, E and EM plus H. An example particle of this type is shown in FIG. 3 as particle Model 9736C which is an iron oxide particle, susceptible to a magnetic or H-Field with a PEG (polyethylene glycol) coating which is susceptible to an E- or EM-Field. For the EM susceptibility of this PEG coated iron ferrite particle, it is only the PEG coating which is susceptible to the electric portion of the EM-Field. The iron ferrite is susceptible to the magnetic of the EM-Field. The antenna array detects the resultant images at step 151.

Figure 1D:
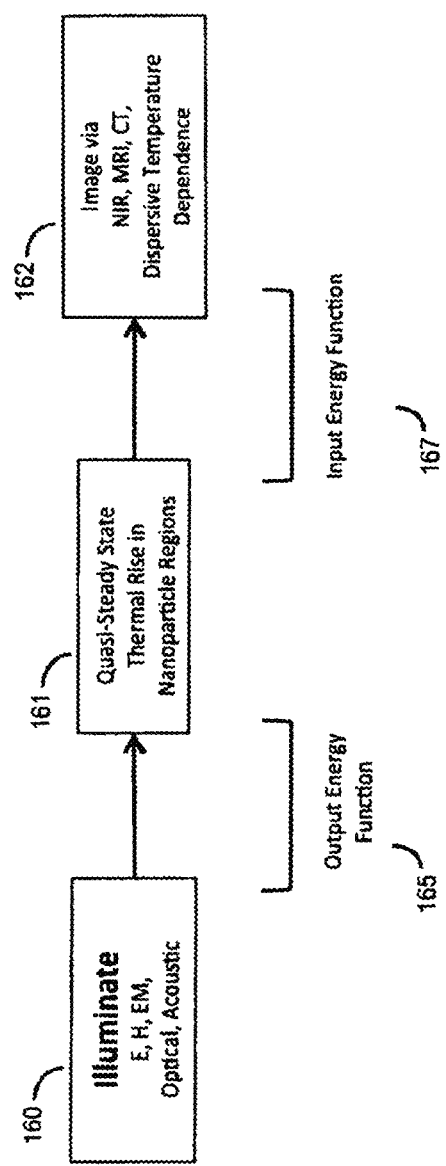
FIG. 1D illustrates a nano-particle imaging method using thermal rise of particles.

As shown in FIG. 1D, the Steady State Thermal Increase Method creates a quasi-steady state thermal signature of nano-particles which, when imbedded in cancer cells, produces a heat or thermal differential to healthy tissue. This thermal signature can be mapped via near infrared means, MRI means, CT means, and so on. Thus, instead of a pulsed waveform for excitation (to, create an acoustical response), a continuous wave or CW waveform could be used to generate a low level but steady state thermal rise in the nano-particle volumetric regions for imaging purposes. Alternative detection means could include the fact that biological materials have a dispersive nature meaning that its permittivity and conductivity vary with temperature. This variance is different for each material and is typically based on the water content of the material. In addition, nano-particles can be designed to have a temperature dependence on its material properties. At step 160, the particles are illuminated, and at step 161, the particles exhibit a steady state temperature increase which is detected at step 162 via various means: near infrared (NIR), Magnetic resonance imaging (MRI), or dispersive delta temperature rise over surrounding tissue. The output energy 165 of the illumination step 160 is converted to heat and is Input Energy at step 167 to System Component 162. In addition, at step 128, the option of using both methods and combining and/or comparing the images generated by each processes to enhance the resolution is a possibility. This step uses two processes to overcome the limitations inherent in each process. This is true for any imaging method herein, where it could be combined with another imaging method to realize an enhanced combined image.

Another method, while not shown, involves using ultrasonic illumination where the particles response to an ultrasonic excitation is different and unique from that of the surrounding tissue. This would be a contrast method for existing ultrasonic imaging techniques. Other detector technologies can be used, with the selection and implementation being a function of the effect that is generated by the target particles when they are activated.

Field Generators

Selection of the field generator will depend on the type of target particle that is appropriate for the desired imaging or treatment sequence. In some cases it will be desirable to utilize a microwave/RF-based method. In these cases where a metallic particle is selected, it is likely that a magnetic (H-Field) excitation (reference System Component 104) will provide the best thermal response. For these cases, an H-Field excitation will likely be realized in the near field of a magnetic radiating element where the magnetic field components will be considerably higher than the electric (E-Field) components. Alternatively, particles that are functionalized to be dipolar will likely realize a greater thermal response in an electric field excitation (reference System Components 103 or 105). One method of dipolar heating involves the process of dielectric heating, where the time varying electric field will cause the target particles to physically rotate, resulting in heat due to intra-molecular heating. For these cases, an E-Field excitation will likely be realized either in the near field of an electric radiating element or in the far field of an EM radiating element.

The Field Generators 103, 104, 105, 118, and 119 are well known components in the industrial and scientific communities and are not described in additional detail herein for the sake of brevity. In general terms, each of these field generators will combine a signal source with a radiating element or other device that couples energy from the signal source to the tissue medium.

It needs to be noted that the mapping of the energy field characteristics to the characteristics of the target particles is critical to enable the precise imaging and treatment of the cancer cells with minimal impact on the surrounding healthy tissue in the living organism. In addition, the mapping of characteristics provides great flexibility and enables the concurrent use of multiple types of target particles and sequences of different detection and treatment procedures.

Similarly, multiple fields can concurrently illuminate the in vivo body or body parts intended to be imaged.

Activated Target Particle Detector

The Activated Target Particle Detector 107 functions to provide feedback to the Energy Field Controller 102. As the target particles are illuminated and generate an effect in response to the incident energy field, the effect can be detected by the use of conventional detector mechanisms. These detectors can be acoustical arrays, microwave antenna arrays, and the like. These arrays are not shown here, but can be seen in example FIGS. 8-10. The feedback to Energy Field Controller 102 could be to increase or decrease the field strength to enable a change in particle temperature, for instance.

For acoustical imaging, the output energy function of laser or RF/microwave pulses are converted to input energy functions in the acoustical range, typically in the ultrasonic frequency range. In this system, it is preferred to use nano-particles that exhibit an enhanced ultra-sonic response by the nano-particle's structural design. An example is a nano-particle that is easily compressed, causing a strong thermal acoustic response, thereby emitting an acoustical signature that stands out from the surrounding tissue. In FIG. 3, such a nano-particle is contemplated as example model number 6754Z in a PEG shell with a surfactant filling in a 3D ellipsoidal shape. While all materials emit an acoustical signature in the presence of an energy pulse, a nano-particle that is less rigid and more pliable emits a stronger acoustical response. Separately, this nano-particle has a strong materials property response due to its unique permittivity and conductivity relative to both cancerous and healthy tissue.

In these applications, electromagnetic energy is applied to a tissue sample infused with the nano-particles to generate heat. The subsequent thermal expansion of both the cells as well as the nano-particles in the tissue produces an acoustic wave that is measured by an array of acoustic sensors. Thermo-acoustic (RF or microwave) and photo-acoustic (laser) imaging are therefore inverse source problems, providing completely different contrast mechanisms than traditional diagnostic imaging techniques. These are shown in FIGS. 1B, upper path, and 1C, left path. The imaging is a result of the system's output energy pulse being converted to a temperature of expansion/contraction of the nano-particle at step 148 which further emits an acoustical signature (system's input energy signature), wherein an ultrasonic array picks up and maps the multi-dimensional extent of the signals at step 150. Since each tissue and corresponding nano-particle emits a different acoustical signature, this enables the differentiation of various tissue types along with the determination of the cancerous region. Specially designed nano-particles, enhanced field strengths, higher excitation frequencies, and higher nano-particle concentrations—all yield enhanced images of breast tissue, where the imaging is done without ionizing radiation, as is done in mammogram x-rays.

Another method of imaging involves differential heating detection as shown in FIG. 1D. Differential heating in cancerous and noncancerous tissue, together with differential heating of nano-particles, for example, can thereby be used to produce an image. Since these different tissues and nano-particles heat at different rates, with differing terminal temperatures, this can be detected by means well known in the art to include using the a priori permittivity and conductivity changes of materials over varying temperatures as shown in FIGS. 1B, lower path, and 1C, right path. These material properties can be detected and vary based on the properties of the material being heating and detected. This is but one of many modes of detection.

Of course, the detection of the differing and time variant temperatures of cancerous and healthy tissue types along with the thermal signature of the nano-particle(s) offer another means of imaging as shown in FIG. 1D. This is clearly one of the preferred embodiments of this approach.

By staying at a low temperature hypothermic region, for example less than 42° C., healthy tissue is not harmed during the imaging and/or treatment process. There are a number of means to control this temperature to stay in the low temperature hypothermic region to include designing the temperature control into the particle. Active feedback is another method where the excitation field strength is modulated based on temperature feedback. By using remote thermal imaging, such as IR, or in vivo probes in the body, say the breast, the temperature of the treatment region can be determined. This feedback can be used to actively manage the illumination function to ensure the cancer is indeed detected without injuring nearby or adjacent healthy tissue. As claimed herein, a treatment modality can be the low level illumination and thermal mapping of where just a slight temperature rise occurs.

The nano-particle derived imaged region can be mapped to the known extent of the cancerous region (from, let's say, a prior MRI or CT scan). If the two regions agree, it means that the thermally sensitive nano-particles (under external field illumination) are in the correct location. However, if the two regions do not correlate with each other, then the tumor's extent has changed or the nano-particles are not in the correct region.

The two key feedback elements of the system are the Activated Target Particle Detector 107 and the Energy Field Controller 102. This is further described in FIGS. 2A and 2B. This feedback between these elements enables enhanced imaging and more precise treatment; for example, other feedback loops are present but these are the significant nodes.

Databases

There are a number of databases which maintain information which is relevant to the disclosed process. These databases as shown herein are for illustrative purposes and the number of databases and their contents can be varied without departing from the spirit and scope of the appended claims. The databases contain information which enable the Energy Field Controller 102 to build an association between the target particles and the desired output that is to be generated by activating the target particles. This correspondence is modulated by the characteristics of the living organism, the depth of the target particles in the living organism, the correspondence between the incident energy field required to produce the desired output, as well as other factors as described herein.

Invasive Agent-to-Detection Characteristics Database

The Invasive Agent-To-Detection/Treatment Characteristics Database 108 maintains data which characterizes the relationship between the invasive agent and the detection/treatment characteristics needed to produce a detectable effect for a selected type of target particle. The data lists the illumination characteristics for a selected nano-particle type required to produce a detectable effect for the selected protocol. As described herein, the effect can be mechanical action, creation of a voltage, thermal excitation, chemical release, and the like. The effect can also target an entire cell or the nucleus of a cell or the cell membrane. In addition, the intensity or magnitude of the effect can vary as a function of the type of cancer being detected. Thus, the Invasive Agent- To-Detection Characteristics Database 108 stores the information required to address all of these characteristics to enable the Energy Field and Target Correlation System 100 to automatically compute and generate the required energy fields.

Patient Data Database

The Patient Data Database 109 maintains patient-specific data which provides data regarding the age, sex, weight, prior surgeries or other conditions relevant to the detection and treatment processes. This data could include factors such as metallic implants, i.e., a pacemaker or an orthopedic screw. These factors may be relevant to the illumination function and energy field control signal generation functions of the Energy Field and Target Correlation System 100 since these factors may have an impact on the energy field generated and the duration of their application.

Empirical And Analytical Data Database

The Empirical And Analytical Data Database 113 maintains information which has been collected via modeling, testing, theoretical computations, and the like. This data represents the experiential knowledge that can be used by the Energy Field and Target Correlation System 100 to automatically set the illumination functions and energy field generator controls. These data sets are created from excitation of particles in highly controlled laboratory environments; additional information is gathered by exciting the particles in a tissue phantom that mimics the characteristics of tissue. Further modeling can be done via computer simulation programs such as Finite Difference Time Domain (FDTD) analysis, which uses sophisticated software and powerful computers to analyze the problem on smaller sized cells which are then aggregated to understand the full problem.

Reflection Characteristics Database and Field Penetration Database

The Reflection Characteristics Database 111 contains data which represents the percentage of an incident signal which is reflected at the interface between two materials, biological, water, air, or the like; and the Field Penetration Database 112 contains data which represents the attenuation of an incident signal as it passes through a selected material.

One factor that the Energy Field Controller 102 must address is the fact that various tissue types have different electromagnetic wave reflection and penetration characteristics. This is particularly true for E-Fields and the electric portion of EM-Field excitations. The magnetic fields of EM excitations are significantly less susceptible, as are H-Fields. This discussion, therefore, centers on the E-Field excitations. In addition, the boundary between one tissue type and another tissue type (or with the atmosphere) provides an interface which can cause reflections of an incident electromagnetic wave. Thus, the incident energy field (electromagnetic wave) must be designed to take into account the type of tissue through which the electromagnetic wave must travel, as well as the depth of tissue through which the electromagnetic wave must penetrate before reaching the implanted target particles.

Inside the body, let's say the breast, there are different material types including fat, connective tissue, fibrous tissue, muscle tissue at the breast wall, cancerous tissue, and so on. In general terms, these materials have characteristics that are specific to each material type, although it should be noted that there are variations in these materials that can be significant from patient to patient. With the exception that water content (and therefore dielectric constant) is typically much higher in tumors and fibrous tissues than fat, it is difficult to identify a discriminatory electrical property that could be used for differentiation of healthy and cancerous tissues. Thus, a contrast agent between healthy and cancerous tissue is essential to enable improved imaging of cancerous tumors. Using a nano-particle of specific properties can dramatically enhance the imaging of breast tissue via electromagnetic means with frequencies in the RF/microwave regions. As previously described and also shown in FIGS. 1B, 1C, and 1D, viable imaging methods can be Acoustic based, or Material Properties based, or Temperature based. Microwave imaging in the 2-3 GHz region has the best balance of imaging resolution and tissue penetration depth, again for E-Field excitation. Optical or laser imaging enables higher contrast but only for cancerous lesions at or near the skin surface. This is due to the penetration depth of laser energy (in fact, similar charts can be developed for lasers such as those used for E-Fields in FIGS. 6 and 7).

In some embodiments of the System, the contrast agent is generally targeted for uptake only by cancerous cells. In general, this is considered a preferred embodiment of the system for the following reasons: (1) less nano-material will be required for uptake only in cancerous cells; (2) uptake by cancerous cells enables direct assessment of the cancerous region; and (3) if treatment were to directly follow the imaging session, the particles are already in place for the treatment. Of course, converse or "negative" imaging, where the particles go to healthy tissue, is another means of imaging.

FIG. 6 illustrates a table of data for E-Fields and the electric portion of EM-Fields that characterizes the reflection coefficient that occurs at the junction between various types of biological tissue types. FIG. 7 illustrates a table of data for E-Fields and the electric portion of EM-Fields that characterizes the depth of penetration of an electromagnetic wave in different tissue types as a function of frequency of the electromagnetic wave. The penetration depth of EM energy into tissue is dependent on the electrical characteristics of the tissue itself, the permittivity ($\epsilon_r$) and the conductivity ($\sigma_r$), as well as the excitation or illumination frequency. FIGS. 6 and 7 were taken from the book *Bioengineering and Biophysical Aspects of Electromagnetic Fields* by Frank S. Barnes and Ben Greenebaum, Third Edition, 2007, page 298 and 299.

Penetration depth is also influenced by how well the incident energy is matched to the layer where a reflection can occur. The reflections at each layer compound the difficulty of delivering energy to a given tumor in the breast which could be embedded in a fat layer or connective tissue layer which compounds the energy delivery problem. For RF/microwave embodiments of the System, the reflection coefficient is defined by the intrinsic impedances of the two layers of tissue types that are touching where a wave must propagate through to reach the desired target of the tumor. The table of FIG. 7 defines the EM field penetration depth for when the value of the field is $e^{-2}$ or 0.1353 times the original level. The penetration depth chart assumes that the wave is introduced in the given material type for the given frequency and travels to the specified distance in the chart where, at the distance, the strength is 0.1353 times the incident wave of 1.0.

Again, magnetic field illumination reduces many of these issues.

For in vivo (in the body) imaging with RF/microwave fields, the first layer of E-Field reflection occurs at the skin-air boundary. Optimally matching the imaging excitation field (output field of the Energy Field and Target Correlation System) requires matching the different intrinsic impedances of the two mediums, air and skin, with a material that acts like a matching transformer. More narrowband matching structures are typically 90 (ninety) electrical degrees in length for the center of the excitation frequency band while more broadband matching structures will have a series of transformers which improve the match. The broadband matching structures are governed by well understood equations to improve the match, where the calculations specify the impedance and phase length of each physical layer of material. The broadband designs can be maximally flat in the pass-band with a preset level of amplitude ripple and so on. The detail of these designs is left to the reader since the process is well understood for those in the art. However, what is novel is that the structure being matched to, say the breast, has a multi-dimensional shape where a given matching layer cannot have air gaps for instance, since air has its own impedance and phase length which would cause unintended reflections and hence imaging errors. Thus, gels or fluids would make desirable matching elements, provided the impedance of the substance is the square root of the two outer layers, skin and air. This ensures that most of the energy goes into the tissue versus being reflected away, unused, at the air-skin boundary layer.

Once the energy is inserted into the body, in vivo, the reflections naturally occur at the fat layer, or the connective tissue layer or ultimately the boundary of the tumor which contains nano-particles. It is difficult to control these reflections of E-field energy. However, it is these very boundary layer reflections that are useful for one of the imaging paradigms disclosed herein, Material Properties Imaging. For the Material Properties imaging methods shown in FIGS. 1B (125, 126) and 1C (147, 149), the reflections off of the differing layers of material properties, particularly off of the nano-particles in the cancer cells, is very desirable and enable one method of imaging.

The table of FIG. 7 defines the EM field penetration depth for when the value of the field is $e^{-2}$ or 0.1353 times the original level. The penetration depth chart assumes that the wave is introduced in the given material type for the given frequency and travels to the specified distance in the chart where, at the distance, the strength is 0.1353 times the incident wave of 1.0.

Target Particle Database

The Target Particle Database 101 maintains a listing of characteristics of at least one type of target particle, from the characteristics of target particles including: size, shape, material composition, density, surface coating, geometry, contents, behavior in the presence of an energy field having predetermined characteristics. In addition, the data can contain a listing of cancer types for which the particular target particle is effective.

FIG. 3 is an example, in table format, of target particle characteristics for nano-particles. The Target Particle Database 101 typically lists characteristics of nano-particles for each of a plurality of nano-particles. For example, for a predetermined model of nano-particle (ex.—9736C) there are relevant characteristics, such as: geometry (cylinder); material which is used to fabricate the nano-particle (Iron-Oxide); dimensions (10 diameter, 75 length); coating (PEG, PolyEthyleneGlycol); concentration (85 picograms per cell (per cancer cell)); excitation response function of 1000 V/m and 15000 A/m. Two fields are used since the particle has two materials which are susceptible to differing field types; the iron ferrite $Fe_3O_4$ is susceptible to a magnetic excitation or H-Field only (given in A/m) while the PEG coating is susceptible to an electric excitation or E-Field only (given in V/m). The frequency for the E-Field is in the S-band range or 2.0 to 4.0 GHz, while the magnetic field is lower in the MHZ range, perhaps as low as 1.0 MHz. These selected frequencies are representative and in no manner are limiting. For example, the magnetic field could be in the 200-300 kHz range, where heating has shown to be very responsive. Frequency selection is chosen based on the area being treated, the particle type, the level of reflections and penetration depth and so on. For instance, selecting the magnetic frequency extremely low puts the magnetic excitation in the Brown region, which does not induce as much energy into the particle, hence heat into the tissue. In the Brown magnetic region, the physical particle must rotate vs. just the magnetic dipole rotating when in the Neel or Rayleigh magnetic regions. For some cases, this may be desirable on the Imaging side of the process, but less desirable on the Treatment side of the process. At frequencies that are not resonant for the particles, frequencies in the MHz or GHz region, the illumination polarization is less important, since particles are resonant in the terahertz region (light spectra). However, the illumination polarization for tissue does have importance and certain tissue artifacts may show up using different polarizations. At optical or laser excitation, the particle shape and size become important since the particle size becomes a substantial part of the illuminating wavelength. In addition, at NIR, IR, optical, or laser frequencies, particles can begin to exhibit meta-material behaviors such as Surface Plasmon Resonances (SPR). The excitation phase can be controlled to ensure that all energy impinging on the skin, for example, arrives in phase so it is additive. In other cases, the electrical phase of the energy can be adjusted to steer the exciting beam over the region to be illuminated, thereby causing a moving energy field over the breast, for example.

Other nano-particles such as 6754Z in FIG. 3 are designed to have an enhanced acoustical response when excited with an energy pulse, RF/microwave or optical. The PEG shell is more easily compressed since it has a surfactant filling (fluid like filling) thereby being more easily compressed/expanded and thereby emitting a stronger acoustical response which is unique from either healthy tissue or cancerous tissue. This material is also unique in terms of its permittivity and conductivity in and E-Field or E(M)-Field. Thus, this nano-particle, similar to the other nano-particles shown in FIG. 3, could be imaged by using both the Acoustical and Material Properties methods in combination, offering a means to combine the two approaches as shown in FIG. 1B at step 128. This offers methodology advantages which overcome limitations of a single mode of imaging.

Nothing herein limits the combinatorial approach of combining imaging methods to realize improved signal to noise ratio and enhanced contrast. For example, the following imaging methods could be combined as a field illumination process, a detection process, and a signal processing/display process: Ultrasonic Detection, Energy Pulse with Acoustical Detection, Materials Properties Detection, and Thermal Detection.

The Target Particle Database defined in System element 101 in FIG. 1A defines the responsiveness of the selected nano-particle to a preferred applied energy field as well as the physical and chemical characteristics of the nano-particle that can be used with a particular invasive agent. For example, a nano-particle of long linear aspect ratio, long and skinny, often has a high affinity for uptake by a cancer cell, yet also is too large or shape specific to be excreted by the cancer cell. To improve this affinity for uptake, a coating of carbodiimide conjugated polyethylene glycol-iron oxide-impregnated dextran can be used as the "composite" deposited on the nano-particle to make it attractive to human breast cancer cells, for instance. This compendium of information for a collection of particles is used by the Energy Field Controller 102 in response to the user identifying the nano-particle and cancer type pairing to create the illumination functions required to detect the presence and locus of the cancer cells in the living organism 110. In addition, the Energy Field Controller 102 computes the sequence of detection energy field controls used to activate the energy field generators.

User Interface

A user interface 106 is also provided to enable a user to select at least one type of target particles that have been infused into a portion of the living organism and identify the portion of a target living organism which contains the selected target particles. This selection also can include a definition of the type of cancer which is being investigated. The User Interface 106 is a well known component in computer systems and is not described in additional detail herein for the sake of brevity. Suffice it to say that it provides the capability to enable a user to define the overall test environment within which the Energy Field and Target Correlation System 100 operates. This interface could be via a keyboard or a Graphical User Interface (GUI), where the GUI is touch screen driven, offering the technician or doctor the ability to more easily and more precisely control the imaging process. Such interfaces are well known and can be implemented using any of a number of commercially available software products.

Energy Fields

An energy field is comprised of fields in the electromagnetic spectrum which range from kilohertz to optical frequencies (terahertz). Radio Frequency (RF) and Microwave energy is contained within this spectrum. The fields can follow or be bounded or be explained by Maxwell's equations and they also can exhibit quantum behavior (light for example exhibits both Maxwell and quantum particle behavior simultaneously). However, it should be noted that the nano-particles that are being excited by the Maxwellian waves may themselves exhibit linear or stepped behavior (which is quantum like in its nature). So, while the illumination function is described by Maxwell's equations, the nano-particle, which is activated under the Maxwellian illumination, may very well exhibit behavior that is non-linear in its nature.

The Maxwellian fields used for illumination functions can generally take the form of three types of fields: an electromagnetic field (EM) which has both types of waves, magnetic and electric, in a spatially orthogonal relationship, an electric field (E) and a magnetic field (H). It is important to recognize that any combination of these three basic field types are possible; and, in fact, may be desirable. Thus, the illumination may be multifold vs. a single illumination type. In addition, the combinations of fields can be arranged to include spatial and temporal domains. It is therefore possible (for example) to have a magnetic field for 2 seconds, followed by an electric field for 5 seconds, in a time or temporal sequential fashion. As another example, 65% of the illumination space could be covered by an electric field while the entire illumination space is illuminated by a magnetic field, all in a concurrent fashion, or a baseline electromagnetic field (EM) could illuminate the target region with a pulsed magnetic field covering the same region. Separately, a given illumination function may only be the electric field, or it may only be the magnetic field, or it may only be an electromagnetic field. Nothing contained herein limits the possibilities or modes of illumination by given field types.

An example of both field types, E and H, being concurrently active is an electromagnetic (EM) field and a further example is an electromagnetic wave that is propagating through the air carrying a signal, with both field types, electric E and magnetic M. In an EM wave, the electric and magnetic fields are spatially orthogonal to each other and propagate together. In contrast, a "pure" electric field has an electric field only and a "pure" magnetic field has a magnetic field only. As already described, an electric field is denoted by the letter E while a magnetic field is denoted by the letter H while an electromagnetic field is denoted by EM.

When a material is illuminated by a given energy field type, the material "absorbs" energy from the field and exhibits that "absorption" by exhibiting a temperature rise or converts the field to an electrical current or exhibits other modes of excitation such as an electro-fluidic force, mechanical motion, and so on. The pairing of the target particle type and the energy field type is managed to control or produce by design a given behavior in the target particle. One desirable illumination energy field-to-target particle trait or property is the presence of a thermal rise in the target particle. When the target particle is placed in an energy field, the target particle, through a mechanism described in the following sections, exhibits a thermal rise to a higher energy state. The thermal rise in the target particle is highly dependent on the pairing of the composition of the target particle (including size, shape, material composition, density, surface coating, geometry, contents, behavior in the presence of an energy field having predetermined characteristics, etc.) with the illumination function, such as an E-Field, H-Field, EM-Field, or optical field. Another desirable trait in the particle under illumination is the propensity to exhibit a strong acoustical response such as that when illuminated via a pulse of energy, RF/microwave or laser. In the case with a thermal response, this delta increase can be mapped and used to differentiate the cancerous tissue with particles vs. healthy tissue. In the second case, acoustical response from material compression/expansion would be used to enhance or differentiate the acoustical signature of both healthy and cancerous tissue from cancerous tissue containing nano-particles.

Target particles contained within a given energy field exhibit certain behaviors. Most important, different target particles and their associated composition respond differently to a given energy field type. In fact, certain target particles do not respond to a specific field type whatsoever; that is, no energy is absorbed by the target particle in that given energy field. An example is a target particle formed of a polymer responds dramatically to an electric field with a sharp temperature rise but has virtually no thermal response to a magnetic field. In contrast and in converse, a target particle formed of $Fe_3O_4$ (iron oxide) exhibits a very steep temperature rise in a magnetic field and has virtually no temperature rise in an electric field. Target particles manufactured from other materials respond in varying degrees to either E- or H-Fields. Target particles manufactured from copper, for example, responds almost equally to either energy field type, E or H. For materials that respond to both E- and H-Fields (such as copper), an optimal excitation source may be an electromagnetic wave (EM) since it simultaneously contains both energy field types in an orthogonal configuration.

Thus, the energy field type used for heating materials needs to be optimally matched to the composition of the target particle. Existing prior art does not recognize the importance of this pairing, that is the pairing of illumination energy field type to composition of the target particle. The Energy Field and Target Correlation System 100 not only recognizes the importance of pairing, but it exploits this property to enhance the thermodynamic and other effects occurring at nano-particles which are illuminated by selected energy fields, thereby optimizing the imaging enhancements: signal to noise and contrast. The Energy Field and Target Correlation System 100 is an intelligent machine, optimizing its illumination function to use feedback methods to enhance images and optimally treat cancer regions.

It is even more important to precisely pair the energy field type for nano-particles because they have virtually no mass, to thermodynamically convert their "absorbed" energy to heating of tissue where the nano-particles are residing. Without this precise pairing of illumination function with nano-particles' material type, the nano-particles do not reach a high enough temperature to thermodynamically transfer their thermal energy to surrounding material (cytoplasm, nucleus, membrane). Separately, the physical composition of the target particle (size, shape, material composition, density, surface coating, geometry, contents, behavior in the presence of an energy field having predetermined characteristics), all make a difference in how the target particle behaves under illumination. The concentration of the energy field strength is an important parameter. In fact, equations show that the heating phenomenon is a function of the energy field strength squared. This is true for both E- and H-Fields, with H-Field illumination being driven by even more complex equations, where sometimes the function could be an H-cubed relationship. Thus, for example, devices that realize "induction heating" methods, which use a very concentrated H-Field, heat metals to melting points while a more distributed H-Field won't have the same heating effect. Therefore, how the field is constructed and presented or delivered to the body or tissue is an additional parameter that is important and controllable.

The prior art has extremely limited understanding of the mechanisms occurring in terms of the thermal heating or other processes of nano-particles in fields of any type. This rather blind approach, presently in use, has no design consideration of energy field/target particle pairing optimization whatsoever. In contrast, the Energy Field and Target Correlation System 100 implements an intelligently defined mapping of target particle composition (size, shape, material composition, density, surface coating, geometry, contents, behavior in the presence of an energy field having predetermined characteristics) with the energy field illumination function. This mapping is essential for the embodiment of a "generic" illumination machine that is target particle agnostic—that is, the "machine" doesn't care what the target particle is made of because the "illumination machine" is architected and designed to illuminate any target particle type, when the target particles are in vivo—inside a human or animal body, or essentially any living organism. In addition, the Energy Field and Target Correlation System 100 is designed to a priori understand how to illuminate a breast cancer image versus a brain cancer image versus imaging a body-wide infection of HIV, or metastatic cancer, which is blood borne.

Positioning Apparatus for Illuminating a Living Organism

Figure 8:
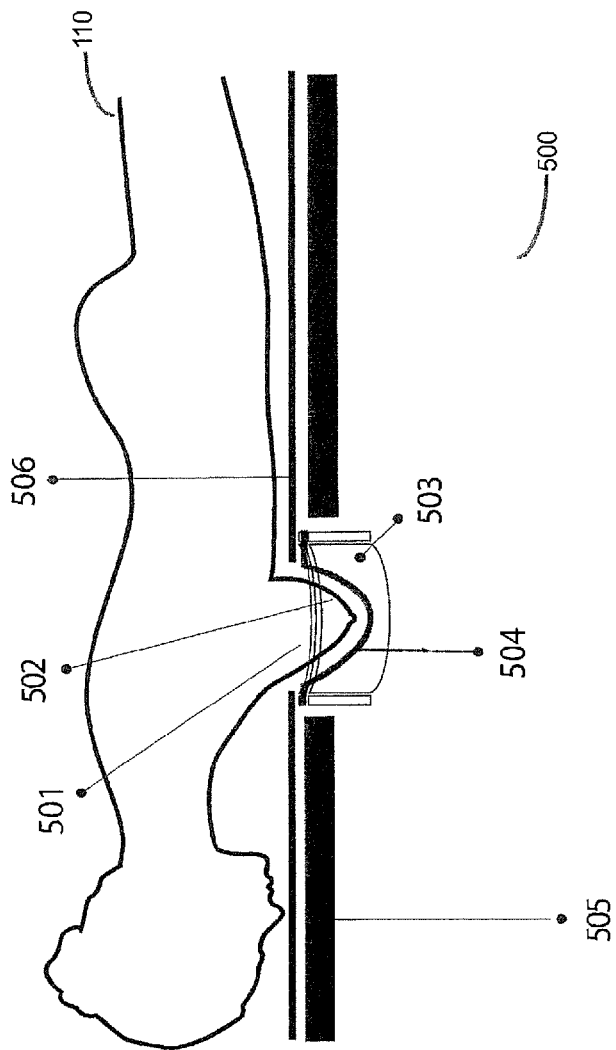
FIG. 8 illustrates a side view of a table that can be used with the Energy Field and Target Correlation System to irradiate human breast tissue in a human laying prone face down on said table.
Figure 9:
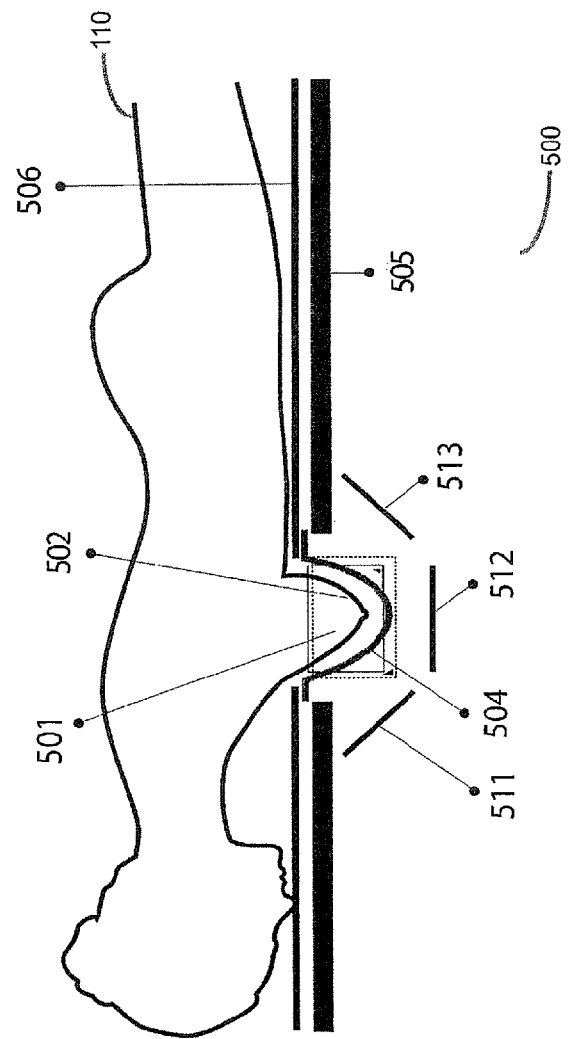
FIG. 9 illustrates a side view of an alternative implementation of a table that can be used with the Energy Field and Target Correlation System to irradiate human breast tissue in a human laying prone face down on said table.
Figure 10:
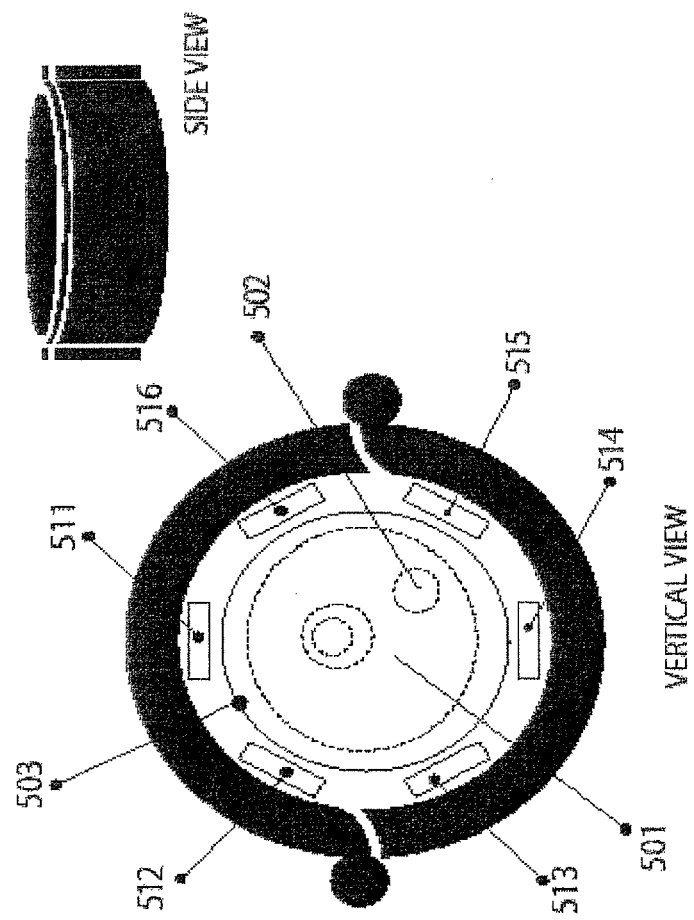
FIG. 10 illustrates additional details of an antenna system that can be used to irradiate human breast tissue in a human laying prone face down on said table.

FIG. 8 illustrates a side view of a table 500 that can be used with the Energy Field and Target Correlation System 100 to irradiate human breast tissue; FIG. 9 illustrates a side view of an alternative implementation of a table 500 that can be used with the Energy Field and Target Correlation System 100 to irradiate human breast tissue; and FIG. 10 illustrates additional details of one type of radiating element that can be used to irradiate human breast tissue using electromagnetic Waves:

As shown in these Figures, the living organism is a woman 110 who is laying face-down on a table 500, in which an aperture is formed to receive her breast 501 for imaging. As shown, the breast 501 contains a tumor 502 that is the subject of the detection process. In order to minimize the reflections caused by the interface between different materials, a field matching substance 503 (FIG. 8) or an RF matching blanket 504 (FIGS. 8 and 9) is provided to encompass the breast 501 when it is in position between the encircling antennas 511-516 (FIG. 11) and the breast 501. The table 500 can be manufactured from an RF absorbing material 505 to prevent the woman's body from stray RF energy that may emanate from the antennas 511-516. Alternatively, or in addition to, the RF absorbing table, an RF shield 506 can be provided to prevent the woman's body 110 from stray RF energy that may emanate from the antennas 511-516. Typically, there is a plurality of radiating elements 511-516 used to implement the antenna, as shown in FIG. 11, and are positioned to encircle the breast 501.

A matching "blanket" or material is one method that can be used to match the electric field or magnetic field or electromagnetic field to the tissue. The skin is the first barrier and has a typical dielectric constant ranging from 1000 at 1 MHz to 80 at 1 GHz. The respective conductivity at 1 MHz is 0.01 S/m and at 1 GHz is 0.8 S/m (Siemens/meter). Moistening the skin with an aqueous solution of NaCl changes the conductivities below 100 MHz but realizes little to no change for the permittivity of wetted skin. If the energy is delivered by free space, as from an antenna, the electric field (EM-Field) needs to be matched to the skin layer to minimize the refection off of the skin boundary condition. A common matching technique would utilize a simple matching "circuit" or material that is 90 electrical degrees long at the center of the selected frequency band. Multiple matching circuits or layers can be used to enhance the bandwidth of the match over a broader frequency range. In general the quarter wave transformer (90 electrical degrees long) matches from one medium to a second medium. Classically, the impedance of the matching medium is the square root of the product of the end point impedances. This impedance matching is less critical for a pure magnetic or H-Field.

In FIG. 9, the radiating elements are contained within devices 511, 512, and 513 are connected physically to the outputs of the Energy Field and Target Correlation System as shown in FIG. 1A at the output arrow lines of generators 103, 104, 105, 118, and 119. These radiating elements take the energy from the field generators and illuminate the breast tissue. In addition, in FIG. 9 at devices 511, 512, and 513, these devices may also contain ultrasonic or acoustical receive detectors to pick up the acoustical signature of the tissue and particles under pulsed excitation. Separately, devices 511, 512, and 513 may also offer a means to detect thermal or temperature differences as described herein. These inputs or receive signals are sent to device 107 in 100 (the Activated Target Particle Detector). Additional detected signals include material properties responses of healthy tissue, cancerous tissue and nano-particles.

In FIG. 10, devices 511, 512, 513, 514, 515, and 516 embody similar functionality. They serve as radiating elements for the generators in Device 100 (103, 104, 105, 118, and 119). These elements may also serve as receiving or pick-up sensors for Activated Target Particle Detector 107. Inputs to Activated Target Particle Detector 107 may include the following:

the acoustical response (from photo or thermal acoustic excitation);

the thermal response (from continuous or pulsed generator excitation);

the materials properties response (from continuous or pulsed generator excitation);

and so on.

In FIG. 10, element 501 is the human breast while element 502 is a cancerous lesion being imaged. The lesion, 502, has nano-particles resident inside the cancer cells offering a contrast agent for the imaging methods described herein: photo/thermal acoustic, materials properties and quasi steady state thermal rise.

Energy Field Controller

The Energy Field Controller 102 automatically selects energy field characteristics, from the characteristics of energy fields including, but not limited to: field type, frequency, field strength, field modulation, repetition frequency, beam size and focal point, to energize the implanted target particle in a selected manner in a portion of the target living organism.

Figure 2A:
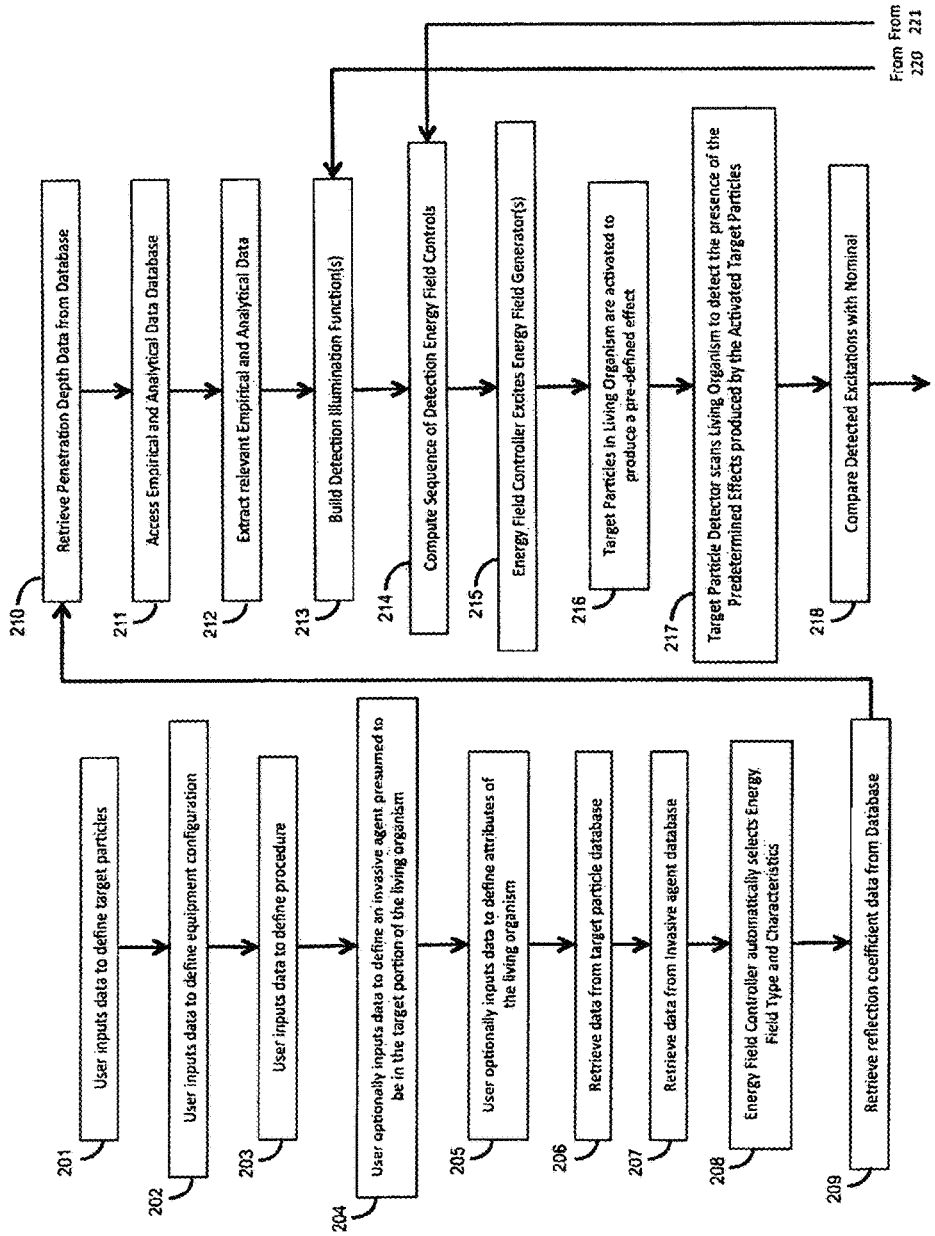
FIGS. 2A-2C illustrate, in flow diagram form, the operation of the Energy Field and Target Correlation System to image and treat invasive agents in a target portion of a living organism, where said system has multiple active feedback loops.
Figure 2B:
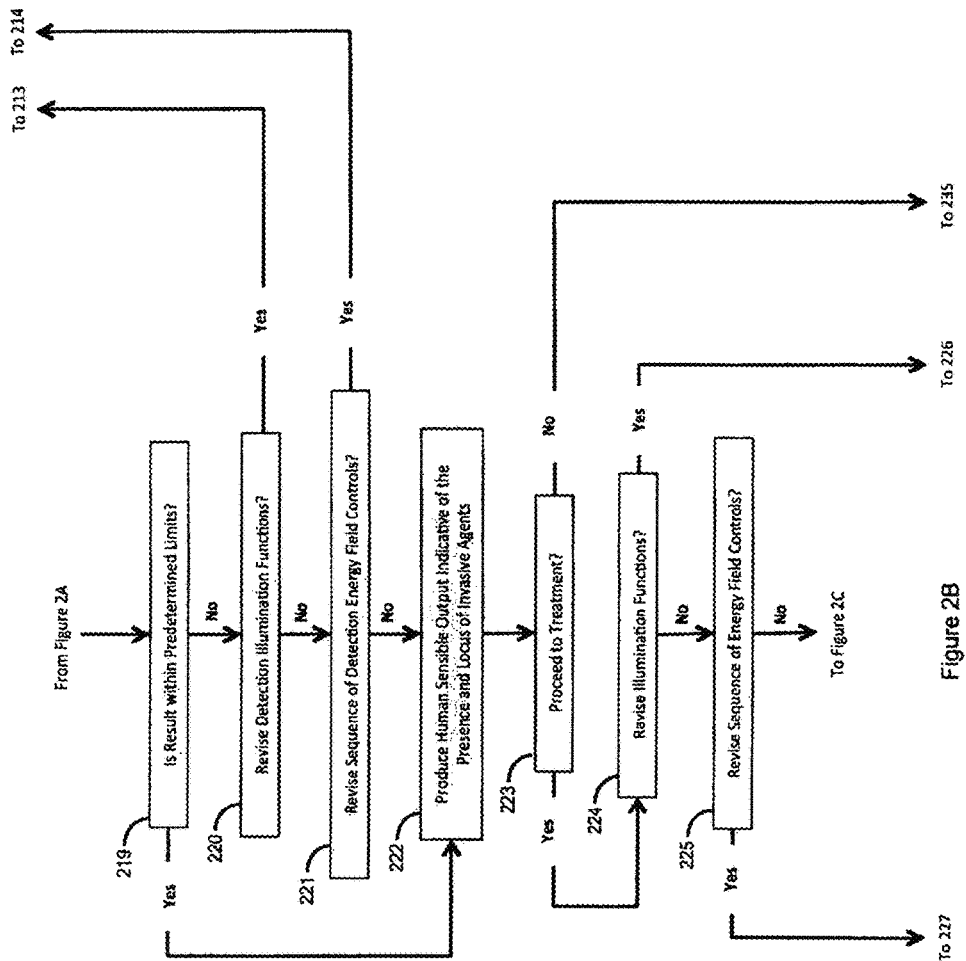
Figure 2C:
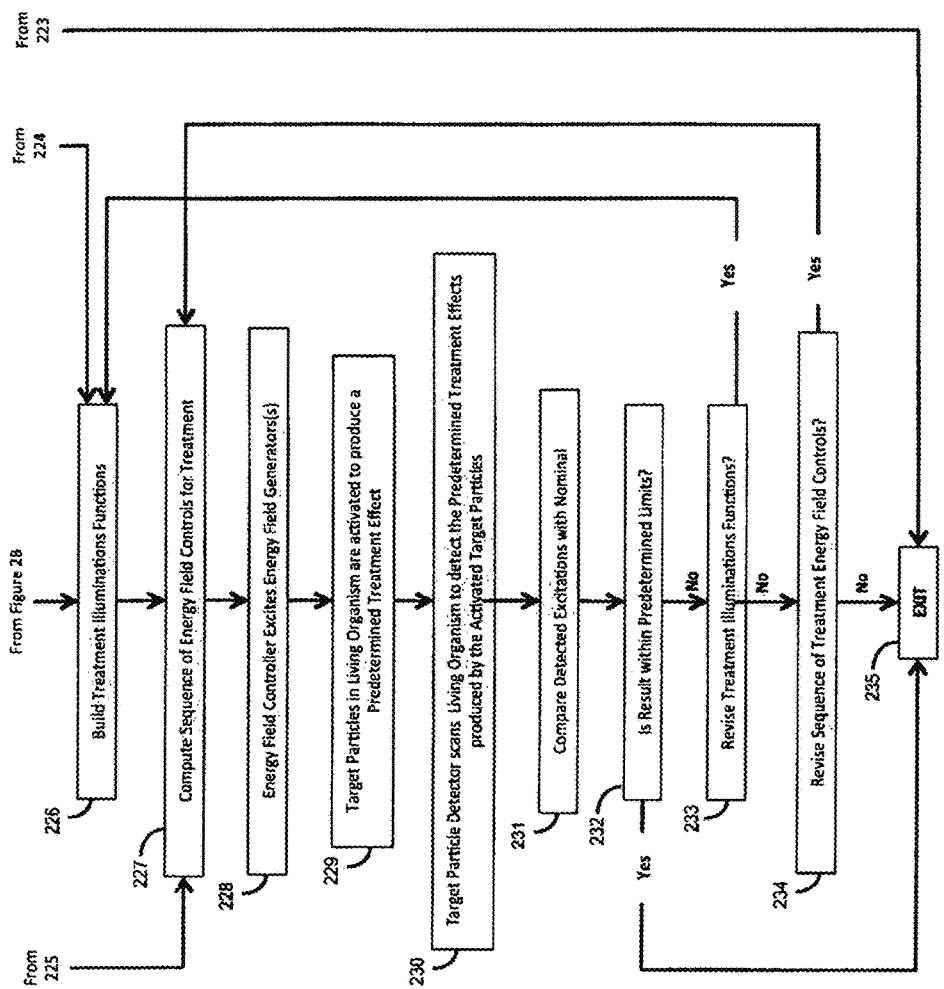

There are a number of logical feedback loops, where the feedback enables the system to have an optimum response. For example, feedback from an image is used to enable optimal treatment. Feedback from a fuzzy image could be enhanced by feedback telling the system to re-image the spatial boundaries of the cancer's extent. Feedback during treatment ensures that particles are heated to the desired temperature, 42° C. for certain applications, and significantly higher to kill the cancer cells. This feedback largely takes place between the Activated Target Particle Detector 107 and the Energy Field Controller 102. FIGS. 2A, 2B, and 2C show numerous feedback, as well as feed-forward, systems-based loops.

FIGS. 2A, 2B, and 2C illustrate in flow diagram form one embodiment of the operation of the Energy Field and Target Correlation System 100 to detect the presence and locus of invasive agents in a target portion of a living organism as well as treat the detected invasive agents. The Energy Field and Target Correlation System 100 receives a set of user provided input data to define the protocol, equipment configuration, living organism as well as the target particles that have been deployed in the living organism. This data is then used by the Energy Field and Target Correlation System 100 to automatically build a set of illumination functions and compute the sequence of energy field controls that are required for the invasive agent detection and treatment protocols. In addition, the Energy Field and Target Correlation System 100 makes use of dynamic feedback to adjust the energy fields during the execution of a selected protocol.

At step 201, the user inputs data via User Interface 106 to the Energy Field and Target Correlation System 100 to define target particles deployed in the living organism 110, such as in the breast of the woman 110. At step 202, the user optionally inputs data via User Interface 106 to the Energy Field and Target Correlation System 100 to define the configuration of the equipment, such as the two table configurations shown in FIGS. 8 and 9. If the equipment configuration is invariant, this step can be skipped. In step 203, the user can also input data via User Interface 106 to the Energy Field and Target Correlation System 100 to define the procedure being executed, such as a detection procedure or a treatment procedure or a combined detection and treatment procedure. The user can then input data into the Energy Field and Target Correlation System 100 at step 204 via User Interface 106 to define an invasive agent (such as breast cancer) presumed to be in the target portion of the living organism 110. At step 205, the user optionally inputs data via User Interface 106 to the Energy Field and Target Correlation System 100 that identifies a selected living organism 110 and the attributes of this living organism 110. This pairing of input information defines the particular application that must be addressed by the Energy Field Controller 102 in automatically generating an illumination protocol that is effective for this application, yet not excessive and potentially damaging to the living organism 110.

In response to these data inputs, at step 206, the Energy Field Controller 102 retrieves data from the Target Particle Database 101 and, at step 207 the Energy Field Controller 102 retrieves data from the Invasive Agent Database 108. This retrieved data, in conjunction with the user input data is used by the Energy Field Controller 102 at step 208 to automatically select energy field characteristics; this also could be set manually, depending on specific circumstances. The energy field characteristics include: field type, frequency, field strength, field modulation, repetition frequency, beam size and focal point, and the like. These energy field characteristics are needed to produce a precisely crafted energy field which is mapped to the target particle characteristics and the target portion of the living organism 110.

At step 209, the Energy Field Controller 102 retrieves reflection coefficient data from the Reflection Characteristic Database 111 and also retrieves penetration depth data at step 210 from the Penetration Depth Database 112 (this is for an E-field component; the H-field excitation is less susceptible to these issues as previously discussed herein). This data enables the Energy Field Controller 102 to account for the particular tissues that the generated energy fields will traverse to reach the deployed target particles. This information is used to adjust the selected energy field characteristics as computed at step 208.

At step 211, the Energy Field Controller 102 accesses the Empirical And Analytical Data Database 113 that maintains information which has been collected via modeling, testing, theoretical computations, and the like. This data represents the experiential knowledge that can be used by the Energy Field and Target Correlation System 100 to automatically set the illumination functions and energy field generator controls. Thus, at step 212, the Energy Field Controller 102 extracts whatever data is relevant to the proposed protocol from the Empirical And Analytical Data Database 113. This step completes the data input, collection, and extraction functions.

At step 213, the energy field controller 102 proceeds to automatically build a set of detection illumination functions which are used to detect the presence and locus of the invasive agents in the living organism. These illumination functions are then used by the Energy Field Controller 102 to compute a sequence of detection energy field controls, which are the control signals used to activate selected Energy Field Generators 103-105, 118, and 119 to produce the illumination energy fields necessary to activate the target particles to produce a desired and detectable effect via the application of the detection energy field controls at step 215.

The energy field generator(s) produce one or more energy fields corresponding to the selected energy field characteristics to illuminate the target portion of the living organism 110; and at step 216, the target particles in the living organism are activated to produce a predetermined effect which can be detected at step 217 by the Activated Target Particle Detector 107 and which enable differentiation between the activated target particles in their associated invasive agents and the surrounding normal cells in the living organism. Then, at step 218, the Energy Field Controller 102 compares the detected excitations with what is expected and, at step 219, determines whether the detected effects are within predetermined limits. In particular, Energy Field Controller 102 can access the data stored in Empirical and Analytical Data Database 113 to compare the detected effects reported by Activated Target Particle Detector 107 with information which has been collected via modeling, testing, theoretical computations, and the like. This collected information is normative data stored in Empirical and Analytical Data Database 113 and can be used to ensure that the detected excitations are within expected limits or whether they represent results which require automatic adjustment of the energy field or even intervention by a human operator. If so, the Activated Target Particle Detector 107 produces a human sensible output at step 222 indicative of the presence and locus of invasive agents as signified by the predetermined effects produced by the activated target particles. If not, processing advances to step 220 where a determination is made whether the illumination functions need to be adjusted by routing back to step 213. If not, processing advances to step 221 where a determination is made as to whether the detection energy field controls need to be adjusted by routing back to step 214. If not, processing advances to step 222. The process then terminates after step 222. An image of the invasive agent, the very output of this invention, is realized at step 222. This image can be used by doctors and treatment teams to understand the spatial extent of cancer and propose likely treatment methods for the said imaged cancer.

At step 224, the energy field controller 102 makes a determination whether the illumination functions need to be adjusted by routing to step 226. If not, processing advances to step 225 where a determination is made whether the detection energy field controls need to be adjusted by routing to step 227. If not, processing advances to step 226. At step 226, the energy field controller 102 proceeds to automatically build a set of treatment illumination functions which are used to treat the invasive agents in the living organism. These treatment illumination functions are then used by the Energy Field Controller 102 at step 227 to compute a sequence of treatment energy field controls, which are the control signals used to activate selected Energy Field Generators 103-105, 118, and 119 at step 228 to produce the treatment illumination energy fields necessary to activate the target particles to produce a desired and detectable effect via the application of the treatment energy field controls at step 229.

The energy field generator(s) produce one or more energy fields corresponding to the selected energy field characteristics to illuminate the target portion of the living organism 110. At step 229, the target particles in the living organism are activated to produce a predefined effect which can be detected at step 230 by the Activated Target Particle Detector 107 and which enable differentiation between the activated target particles in their associated invasive agents and the surrounding normal cells in the living organism. Then at step 231, the Activated Target Particle Detector 107 compares the detected excitations with what is expected and at step 232 determines whether the detected effects are within predetermined limits. As an example, if the image shows the entire breast as being cancerous, there is likely an error somewhere that needs to be resolved. If so, the Activated Target Particle Detector 107 exits at step 235. If not, processing advances to step 233 where a determination is made whether the treatment illumination functions need to be adjusted by routing back to step 226. If not, processing advances to step 234 where a determination is made whether the treatment energy field controls need to be adjusted by routing back to step 227. If not, processing advances to step 235 and the protocol is terminated. An image of the invasive agent, the very output of this invention, is realized at step 235. This image can be used by doctors and treatment teams to understand the spatial extent of cancer and propose likely treatment methods for the said imaged cancer.

Summary

Thus, the Energy Field and Target Correlation System automatically computes a set of illumination functions and energy field controls in response to a user providing inputs that define the nano-particles, living organism, and cancer that is the target of the generated energy fields. This process enables enhanced imaging of cancerous or invasive tissue types embedded in healthy tissue without using ionizing radiation (x-rays) such as that in mammograms. The automatic customization of the energy fields provides a level of control and precision presently unavailable in the art.

What is claimed as new and desired to be protected by Letters Patent of the United States is:

1. A cancer treatment system comprising:
   a plurality of magnetic particles for insertion into a patient;
   a magnetic field generator generating an AC magnetic field having a maximum magnetic field intensity; and
   a temperature detector, in communication with the magnetic field generator, the temperature detector configured with a probe to detect the temperature of the magnetic particles located within the patient;
   wherein said magnetic field generator adjusts the maximum magnetic field intensity in response to the temperature of the magnetic particles so as to maintain the magnetic particles at a predetermined temperature.

2. The cancer treatment system of claim 1 wherein the magnetic particles respond to exposure to the AC magnetic field with the production of heat.

3. The system of claim 1 wherein the temperature detector senses changes in tissue permittivity.

4. The system of claim 1 wherein the temperature detector senses changes in tissue conductivity.

5. The system of claim 1 wherein the predetermined temperature is substantially 42 degrees Celsius.

6. The system of claim 1 wherein the AC magnetic field has a frequency of 200 kHz - 1 Mhz.

7. A method operating a cancer treatment system for use in heating magnetic particles, which are inserted into patient in a manner so as to destroy cancer tissue, the method comprising the steps of:
   inserting a plurality of magnetic particles into the patient;
   positioning the patient for exposure to an AC magnetic field having a maximum intensity;
   generating an AC magnetic field to excite the magnetic particles to a predetermined temperature;
   measuring the temperature of the excited target particles within the patient; and
   adjusting the maximum AC magnetic field in response to the measured temperature of the excited target particles so as to maintain the temperature of the target particles at a predetermined temperature.

8. The method of claim 7 wherein the predetermined temperature is substantially 42 degrees Celsius.

9. The method of claim 7 wherein the AC magnetic field has a frequency of 200 kHz - 1 Mhz.

* * * * *